US008981062B2

(12) United States Patent
Krasnoperov et al.

(10) Patent No.: US 8,981,062 B2
(45) Date of Patent: *Mar. 17, 2015

(54) POLYPEPTIDE COMPOUNDS FOR INHIBITING ANGIOGENESIS AND TUMOR GROWTH

(75) Inventors: Valery Krasnoperov, South Pasadena, CA (US); Nathalie Kertesz, Agoura Hills, CA (US); Ramachandra Reddy, Conshohocken, PA (US); Parkash Gill, Agoura Hills, CA (US); Sergey Zozulya, San Diego, CA (US)

(73) Assignee: Vasgene Theapeutics, Inc, Los Angeles, CA (US)

( * ) Notice: Subject to any disclaimer, the term of this patent is extended or adjusted under 35 U.S.C. 154(b) by 798 days.

This patent is subject to a terminal disclaimer.

(21) Appl. No.: 13/153,692
(22) Filed: Jun. 6, 2011
(65) Prior Publication Data

US 2013/0344075 A1 Dec. 26, 2013

Related U.S. Application Data

(63) Continuation of application No. 10/592,284, filed as application No. PCT/US2005/008280 on Mar. 11, 2005, now Pat. No. 7,977,463, which is a continuation-in-part of application No. 10/949,720, filed on Sep. 23, 2004, now Pat. No. 7,381,410, and a continuation-in-part of application No. 10/800,350, filed on Mar. 12, 2004, now Pat. No. 7,862,816.

(60) Provisional application No. 60/612,908, filed on Sep. 23, 2004.

(51) Int. Cl.
| C07K 16/00 | (2006.01) |
| C07K 16/40 | (2006.01) |
| C07K 16/28 | (2006.01) |
| C07K 16/30 | (2006.01) |
| A61K 39/00 | (2006.01) |

(52) U.S. Cl.
CPC ............. *C07K 16/40* (2013.01); *C07K 16/2866* (2013.01); *C07K 16/30* (2013.01); *A61K 2039/505* (2013.01); *C07K 2316/95* (2013.01); *C07K 2316/96* (2013.01)
USPC ...................................... 530/388.1

(58) Field of Classification Search
None
See application file for complete search history.

(56) References Cited

U.S. PATENT DOCUMENTS

| 5,264,209 A | 11/1993 | Mikayama et al. |
| 5,512,591 A | 4/1996 | Halperin et al. |
| 5,624,899 A | 4/1997 | Bennett et al. |
| 5,635,177 A | 6/1997 | Bennett et al. |
| 5,693,762 A | 12/1997 | Queen et al. |
| 5,770,599 A | 6/1998 | Gibson |
| 5,795,734 A | 8/1998 | Flanagan et al. |
| 5,824,303 A | 10/1998 | Bartley et al. |
| 5,864,020 A | 1/1999 | Bennett |
| 6,015,711 A | 1/2000 | Olson et al. |
| 6,303,769 B1 | 10/2001 | Cerretti |
| 6,413,730 B1 | 7/2002 | Holland |
| 6,423,685 B1 | 7/2002 | Drummond et al. |
| 6,440,954 B1 | 8/2002 | Haber et al. |
| 6,479,459 B1 | 11/2002 | Cerretti |
| 6,492,140 B2 | 12/2002 | Cerretti |
| 6,514,497 B1 | 2/2003 | Briskin et al. |
| 6,579,683 B2 | 6/2003 | Wang et al. |
| 6,673,343 B2 | 1/2004 | Bennett et al. |
| 6,864,227 B1 | 3/2005 | Wang et al. |
| 6,887,674 B1 | 5/2005 | Wang et al. |
| 6,916,625 B2 | 7/2005 | Wang et al. |
| 6,926,898 B2 | 8/2005 | Rosen et al. |
| 7,163,808 B2 | 1/2007 | Anderson et al. |
| 7,576,052 B2 | 8/2009 | Kahn et al. |
| 7,585,967 B2 | 9/2009 | Reddy et al. |
| 7,700,297 B2 | 4/2010 | Wang et al. |
| 7,741,272 B2 | 6/2010 | Wang et al. |
| 7,862,816 B2 | 1/2011 | Krasnoperov et al. |
| 2002/0103358 A1 | 8/2002 | Cerretti et al. |
| 2002/0142444 A1 | 10/2002 | Caras |
| 2003/0157712 A1 | 8/2003 | Daniel et al. |
| 2004/0110150 A1 | 6/2004 | Koller et al. |
| 2004/0136983 A1 | 7/2004 | Aguet |
| 2004/0234520 A1 | 11/2004 | Aguet et al. |
| 2004/0247592 A1 | 12/2004 | Roifman et al. |
| 2005/0049176 A1 | 3/2005 | Kiener et al. |
| 2006/0204512 A1 | 9/2006 | Krasnoperov et al. |
| 2006/0241027 A1 | 10/2006 | Hauser et al. |
| 2007/0207952 A1 | 9/2007 | Silva et al. |

FOREIGN PATENT DOCUMENTS

| EP | 0 442 724 | 8/1991 |
| EP | 0 633 315 A2 | 1/1995 |
| EP | 0 999 278 | 5/2000 |

(Continued)

OTHER PUBLICATIONS

Bennett et al (JBC, 1994, 269: 14211-14218).*
Adams, R.H., et al., "Eph Receptors and Ephrin Ligands: Essential Mediators of Vascular Development," Trends. Cardiovasc. Med., 10:183-188 (2000).
Adams, R.H., et al., "Roles of ephrinB ligands and EphB receptors in cardiovascular development: demarcation of arterial/venous domains, vascular morphogenesis, and sprouting angiogenesis," Genes Dev. 13:295-306 (1999).
Andres, A. C. et al., "Expression of two novel eph-related receptor protein tyrosine kinases in mammary gland development and carcinogenesis," Oncogene, 9:1461-1467 (1994).
Asahara, T. et al., "Isolation of Putative Progenitor Endothelial Cells for Angiogenesis," Science, 275:964-967 (1997).
Batlle, E., et al., "EphB receptor activity suppresses colorectal cancer progression," Nature, 435(23):1126-1130 (2005).
Benjamini et al., Immunity, A Short Course, 2nd Ed., Wiley-Liss pub. p. 40 (1992).
Bennett et al., "Extracellular Domain-IgG Fusion Proteins for Three Human Natriuretic Peptide Receptors," The Journal of Biological Chemistry, vol. 266(34), pp. 23060-23067 (1991).

(Continued)

*Primary Examiner* — Sean Aeder
(74) *Attorney, Agent, or Firm* — Craig A Crandall

(57) ABSTRACT

In certain embodiments, this present invention provides polypeptide compositions (e.g., antibodies and antigen binding portions thereof that bind to EphB4), and methods for inhibiting EphB4 activity. In other embodiments, the present invention provides methods and compositions for treating cancer or for treating angiogenesis-associated diseases.

23 Claims, 13 Drawing Sheets

(56) References Cited

FOREIGN PATENT DOCUMENTS

| | | |
|---|---|---|
| WO | WO 93/00425 | 1/1993 |
| WO | WO 93/15201 | 8/1993 |
| WO | WO 94/10202 | 5/1994 |
| WO | WO 94/11020 | 5/1994 |
| WO | WO 95/27061 | 10/1995 |
| WO | WO 96/01839 | 1/1996 |
| WO | WO 96/02645 | 2/1996 |
| WO | WO 96/03043 | 2/1996 |
| WO | WO 96/09384 | 3/1996 |
| WO | WO 96/13518 | 5/1996 |
| WO | WO 96/23000 | 8/1996 |
| WO | WO 96/26958 | 9/1996 |
| WO | WO 96/36713 | 11/1996 |
| WO | WO 97/09427 | 3/1997 |
| WO | WO 97/23629 | 7/1997 |
| WO | WO 97/43960 | 11/1997 |
| WO | WO 97/44453 | 11/1997 |
| WO | WO 98/01548 | 1/1998 |
| WO | WO 98/43960 | 10/1998 |
| WO | WO 98/45331 | 10/1998 |
| WO | WO 98/45708 | 10/1998 |
| WO | WO 99/08696 | 2/1999 |
| WO | WO 99/17796 | 4/1999 |
| WO | WO 99/52541 | 4/1999 |
| WO | WO 99/45026 | 9/1999 |
| WO | WO 00/24413 | 5/2000 |
| WO | WO 00/30673 | 6/2000 |
| WO | WO 01/49743 | 7/2001 |
| WO | WO 01/81377 | 11/2001 |
| WO | WO 02/11785 | 2/2002 |
| WO | WO 02/26827 | 4/2002 |
| WO | WO 02/058538 | 8/2002 |
| WO | WO 02/061055 | 8/2002 |
| WO | WO 02/063037 | 8/2002 |
| WO | WO 02/079382 | 10/2002 |
| WO | WO 02/102854 | 12/2002 |
| WO | WO 02/102972 | 12/2002 |
| WO | WO 02/102973 | 12/2002 |
| WO | WO 03/000113 | 1/2003 |
| WO | WO 03/004057 A1 | 1/2003 |
| WO | WO 03/094859 | 11/2003 |
| WO | WO 2004/014292 | 2/2004 |
| WO | WO 2004/020468 | 3/2004 |
| WO | WO 2004/024773 A1 | 3/2004 |
| WO | WO 2004/080425 | 9/2004 |
| WO | WO 2004/091375 | 10/2004 |
| WO | WO 2005/048917 | 6/2005 |
| WO | WO 2005/051307 | 6/2005 |
| WO | WO 2005/090406 | 9/2005 |

OTHER PUBLICATIONS

Bennett, B. D. et al., "Molecular cloning of a ligand for the EPH-related receptor protein-tyrosine kinase Htk," Proc. Natl. Acad. Sci. USA, 92:1866-1870 (1995).

Bennett, B.D., et al., "Cloning and Characterization of HTK, a Novel Transmembrane Tyrosine Kinase of the EPH Subfamily," The Journal of Biological Chemistry, 269(19): 14211-14218 (1994).

Berclaz, G., et al., "Activation of the receptor protein tyrosine kinase EphB4 in endometrial hyperplasia and endometrial carcinoma," Ann Oncol., 14:220-226 (2003).

Berclaz, G., et al., "Expression of the receptor protein tyrosine kinase myk-1/htk in normal and malignant mammary epithelium," Biochem Biophys Res Commun., 24;226:869-875 (1996).

Berclaz, G., et al., "Loss of EphB4 receptor tyrosine kinase protein expression during carcinogenesis of the human breast," Oncology Reports, 9(5):985-989, (2002).

Bergemann, A. D. et al., "ELF-2, a New Member of the Eph Ligand Family is Segmentally Expressed in Mouse Embryos in the Region of the Hindbrain and Newly Forming Somites," Molecular and Cellular Biology, 15(9):4921-4929 (1995).

Bos et al., "PD153035, a Tyrosine Kinase Inhibitor, Prevents Epidermal Growth Factor Receptor Activation and Inhibitors Growth of Cancer Cells in a Receptor Number-dependent Manner," Clinical Cancer Research, 3:2099-2106 (1997).

Bowie et al., "Deciphering the message in protein sequences: tolerance to amino acid substitutions," Science, vol. 247(4948), pp. 1306-1310 (1990).

Boyd, W.A., et al., "Isolation and Characterization of a Novel Receptor-type Protein Tyrosine Kinase (hek) from a Human Pre-B Cell Line," The Journal of Biological Chemistry, 267(5):3262-3267 (1992).

Brambilla, R., et al., "Membrane-bound LERK2 ligand can signal through three different Eph-related receptor tyrosine kinases," EMBO J., 14:3116-3126 (1995).

Brehmer et al., "Cellular Targets of Gefitinib," Cancer Research, 65(2):379-382 (2005).

Breier et al., Angiogenesis in Embryos and Ischemic Diseases, Thrombosis and Haemostosis 78(1):678-683 (1997).

Bruckner et al., "Tyrosine Phosphorylaton of Transmembrane Ligands for Eph Receptors," Science, 275:1640-1643 (1997).

Bruhl, T., et al., "Homeobox A9 Transcriptionally Regulates the EphB4 Receptor to Modulate Endothelial Cell Migration and Tube Formation," Circ. Res., 743-751 (2004) [Epub ahead of print] DOI 10.1161/01res0000120861.27064.09.

Burgess et al., "Possible dissociation of the heparin-binding and mitogenic activities of heparin-binding (acid fibroblast) growth factor-1 from its receptor-binding activities by site-directed mutagenesis of a single lysine residue," Journal of Cell Biology, vol. 111, pp. 2129-2138 (1990).

Caplen, N.J., "RNAI as a Gene Therapy Approach," Expert Opin. on Biol. Therapy, 3(4):575-586, (2003).

Carbone, M., et al., "The pathogenesis of mesothelioma," Semin. Oncol., 29(1):2-17 (2002).

Chang, M.W., et al., "Adenovirus-Mediated Over-Expression of the Cyclin/Cyclin-Dependent Kinase Inhibitor, p21 Inhibits Vascular Smooth Muscle Cell Proliferation and Neointima Formation in the Rat Carotid Artery Model of Balloon Angioplasty," J. Clin. Invest., 96:2260-2268 (1995).

Cheng, N., et al., "The ephrins and Eph receptors in angiogenesis," Cytokine & Growth Factor Reviews, 13:75-85 (2002).

Chrencik et al., Three-dimensional Structure of the EphB2 Receptor in Complex with an Antagonistic Peptide Reveals a Novel Mode of Inhibition, J. Biol. Chem. 282: 36505-36513 Sep. 26, 2007 Epub.

Coffman, K.T., et al., "Differential EphA2 Epitope Display on Normal versus Malignant Cells," Cancer Research, 63:7907-7912 (2003).

Cowan, C.A., et al., "Ephrins in reverse, park and drive," Trends in Cell Biology, 12(7):339-346 (2002).

Cromer et al., "Identification of genes associated with tumorigenesis and metastatic potential of hypopharyngeal cancer by microarray analysis," Oncogene, Basingstoke, Hants, GB, 23(14):2484-2498, (2004).

Davis, S., et al., "Ligands for EPH-related receptor tyrosine kinases that require membrane attachment or clustering for activity," Science, 266(5186):816-819 (1994).

Dermer, G., "Another Anniversary for the War on Cancer," Bio/Technology, 12:320 (1994).

Dodelet, V.C. et al., "Eph Receptors and Ephrin Ligands: Embryogenesis to Tumorigenesis," Oncogene, 19(49): 5614-19 (2000).

Durbin, L., et al., "Eph signaling is required for segmentation and differentiation of the somites," Genes & Development, 12:3096-3109 (1998).

Easty et al., "Abnormal Protein Tyrosine Kinase Gene Expression During Melanoma Progression and Metastasis," Int. J. Cancer, 60:129-136 (1995).

Easty et al., "Cytokine B61 as a growth factor for metastatic melanomas and increasing expression of its receptor ECK during melanoma progression," Proceedings of the American Association for Cancer Research, 35(356) (1994) abstract only.

Easty, et al., "Expression of Eck and Lerk-1 During Melanoma Progression," P137 St. Georges Hospital Medical School, London, JK and Western Infirmary, Glasgow, UK, Br. J. Cancer 78(1):137 (1998).

(56) References Cited

OTHER PUBLICATIONS

Fabes et al., "Accumulation of the Inhibitory Receptor EphA4 May Prevent Regeneration of Corticospinal Tract Axons Following Lesion," Eur. J. Neurosci., 23(7):1721-1730 (2006) (Abstract).
Feldman, L.J., et al., "Perspectives of Arterial Gene Therapy for the Prevention of Restenosis," Cardiovasc. Res., 32:194-207 (1996).
Folkman et al., "Angiogenic Factors," Science, 235:442-447 (1987).
Folkman, "Angiogenesis in cancer, vascular, rheumatoid and other disease," Nature Medicine, 1:27-31, (1995).
Folkman, J. et al., "Blood Vessel Formation: What is Its Molecular Basis?" Cell, 87:1153-1155 (1996).
Folkman, J., "Angiogenic Therapy of the Human Heart," Circulation, 97(7): 628-29 (1998).
Folkman, J., "Antiangiogenic Gene Therapy," Proc. Natl. Acad. Sci. USA., 95:9064-66 (1998).
Folkman, J., "Fighting Cancer by Attacking Its Blood Supply," Sci. Am., 275(3): 150-54 (1996).
Fox et al., Invasiveness of breast carcinoma cells and transcript profile: Eph receptors and ephrin ligands as molecular markers of potential diagnostic and prognostic application, Biochim. Biophys. Res. Comm. 318(4):882-892 (2004).
Freshney, R. Ian, *Culture of Animal Cells: A Manual of Basic Technique*, pp. 3-4 (1983).
Fuller, T., et al., "Forward EphB4 signaling in endothelial cells controls cellular repulsion and segregation from ephrinB2 positive cells," J. Cell Sci., 116:2461-2470 (2003).
Gale, N.W. et al., "Growth Factors Acting Via Endothelial Cell-Specific Receptor Tyrosine Kinases: VEGFs, Angiopoietins, and Ephrins in Vascular Development," Genes Dev., 13:1055-66 (1999).
Gale, N.W., et al., "Ephrin-B2 Selectively Marks Arterial Vessels and Neovascularization Sites in the Adult, with Expression in Both Endothelial and Smooth-Muscle Cells," Dev. Biol., 230: 151-160 (2001).
GenBank Accession No. P52803. (1996).
Genetech's Response to Final Office Action on U.S. Appl. No. 09/442,898, filed Mar. 29, 2002.
Gerety, S.S., et al., "Symmetrical mutant phenotypes of the receptor EphB4 and its specific transmembrane ligand ephrin-B2 in cardiovascular development," Mol. Cell, 4:403-414 (1999).
Gill, P.S., et al., "Epidemic (AIDS-related) Kaposi's sarcoma: Epidemiology pathogenesis and treatment," AIDS Updates, (7) 1-11 (1994).
Glassberg et al., "Cultured endothelial cells derived from the human iliac arteries," In Vitro, 18:859-866 (1982).
Goetz et al., "Long-term serial cultivation of arterial and capillary endothelium from adult bovine brain," In Vitro Cellular and Developmental Biology, 21:172-180 (1985).
Gura, T., "Systems for Identifying New Drugs are Often Faulty," Science, 278:1041-1042 (1997).
Guzman, R.J., et al., "In Vivo Suppression of Injury-Induced Vascular Smooth Muscle Cell Accumulation Using Adenovirus-Mediated Transfer of the Herpes Simplex Virus Thymidine Kinase Gene," Proc. Natl. Acad. Sci. USA, 91:10732-10736 (1994).
Hafner et al., "Differential Gene Expression of Eph Receptors and Ephrins in Benign Human Tissues and Cancers," Clinical Chemistry, 50(3):490-499 (2004).
Hafner, et al., "Loss of Eph B6 expression in metastatic melanoma," International Journal of Oncology, 23:1553-1559 (2003).
Hamada, K., Distinct roles of ephrin-B2 forward and EphB4 reverse signaling in endothelial cells, Arterioscler. Thromb. Vasc. Biol., 23:190-197 (2003).
Hausner, C., "Organogenesis Vascular Graft Becomes Physiologically-Responsive Living Tissue After Implantation [online]," Nature Biotechnol., (1999).
He et al., "The Effect of Soluble EphrinB4 Receptor on Laser-Induced Choroidal Neovascularization," IOVS, 45:U804 (2004).
Henkemeyer, M., et al., "Nuk Controls Pathfinding of Commissural Axons in the Mammalian Central Nervous System," Cell, 86:35-46 (1996).

Himanen et al., Crystal structure of the ligand-binding domain of the receptor tyrosine kinase EphB2, Nature 396:486-491 (1998).
Himanen, J.P., et al., "Eph receptors and ephrins," Intl. J. Biochem. & Cell Bio., 35:130-134 (2003).
Himanen, J.P., et al., "Eph signaling: a structural view," Trends in Neurosciences, 26(1):46-51 (2003).
Hirai, H., "A novel putative tyrosine kinase receptor encoded by the eph gene," Science, 238:1717-1720 (1987).
Holder and Klein, Eph Receptors and ephrins: effectors of morphogenesis, Development 126(10):2033-2041 (1999).
Inada et al., Selective expression of the receptor tyrosine kinase, HTK, on human erythroid progenitor cells, Blood 89(8):2757-2765 (1997).
Indolfi, C., et al., "Inhibition of Cellular ras Prevents Smooth Muscle Cell Proliferation After Vascular Injury In Vivo," Nature Med., 1(6):541-545 (1995).
Kashiwa-Kawai, A variant transcript encoding a soluble truncated form of the human Eph receptor family tyrosine kinase, EphB4v is generated by alternative splicing, Scientific Reports of Meiji Seika Kaisha, 1998, vol. 37 abstract.
Kenyon, B.M., et al., "A Model of Angiogenesis in the Mouse Cornea," Invest Ophthalmol. Vis. Sci., 37:1625-1632 (1996).
Keogh, M-C, et al., "Design of a Muscle Cell-Specific Expression Vector Utilising Human Vascular Smooth Muscle ?—Actin Regulatory elements," Gene Therapy, 6:616-628 (1999).
Kertesz et al., "The soluble extracellular domain of EphB4 (sEphB4) antagonized EphB4-EphrinB2 interaction, modulates angiogenesis, and inhibits tumor growth," Blood 107(6):2330-2338 (2006).
Kiessig et al., "Application of a green fluorescent fusion protein to study protein-protein interactions by electrophoretic methods," Electrophoresis, vol. 22, pp. 1428-1435 (2001).
Kitamura et al., "Chemical Engineering of the Monoclonal Antibody A7 by Polyethylene Glycol for Targeting Cancer Chemotherapy", Cancer Research, vol. 51, pp. 4310-4315 (1991).
Kiyokawa, E., et al., "Overexpression of ERK, an EPH family receptor protein tyrosine kinase, in various human tumors," Cancer Res., 54:3645-3650 (1994).
Kullander, K., et al., "Mechanisms and functions of eph and ephrin signalling," Nature Reviews, Molecular Cell Biology, 3:475-486 (2002).
Lackmann, et al., "Distinct Subdomains of the EphA3 Receptor Mediate Ligand Binding and Receptor Dimerization," The Journal of Biological Chemistry, 273 (32):20228-20237 (1998).
Leger et al., "Identification of CJC-1131-Albumin Bioconjugate as a Stable and Bioactive GLP-1/7-36 Analog," Biorganic & Med. Chem. Ltrs 14:4395-4398 (2004).
Li, J., et al., "Expression of the SM22x Promoter in Transgenic Mice Provides Evidence for Distinct Transcriptional Regulatory Programs in Vascular and Visceral Smooth Muscle Cells," J. Cell Biol., 132:849-59 (1996).
Lin, P., et al., "Antiangiogenic Gene Therapy Targeting the Endothelium-Specific Receptor Tyrosine Kinase Tie2," Proc. Natl. Acad. Sci., USA, 95:8829-8834 (1998).
Magal et al., Rapid Communication: B61, a Ligand for the Eck Receptor Protein-Tyrosine Kinase, Exhibits Neuroptrophic Activity in Cultures of Rat Spinal Cord Neurons, J. Neuroscience Res. 43:735-744 (1996).
Magal, et al., "B61, a Ligand for the Eck Receptor Protein-Tyrosine Kinase, Exhibits Neurotrophic Activity in Cultures of Rat Spinal Cord Neurons," Journal of Neuroscience Research, 43:735-744 (1996).
Martiny-Baron et al., Inhibition of Tumor Growth and Angiogenesis by Soluble EphB4, Neoplasia 6(3):248-257 (2004).
Maru, et al., "Evolution, Expression, and Chromosomal Location of a Novel Receptor Tyrosine Kinase Gene, eph," Molecular and Cellular Biology, 8(9):3770-3776 (1998).
Maru, et al., "Overexpression confers an oncogenic potential upon the eph gene," Oncogene, 5:445-447 (1990).
Mellitzer, G., et al., "Control of cell behavior by signalling through Eph receptors and ephrins," Neurobiology, 10:400-408 (2000).
Mellitzer, G., et al., "Eph Receptors and Ephrins Restrict Cell Intermingling and Communication," Nature, 400:77-82 (1999).

(56) References Cited

OTHER PUBLICATIONS

Miki et al., "Association of Ash/Grb-2 with Dynamin through the Src Homology 3 Domain", The Journal of Biological Chemistry, vol. 269(8), pp. 5489-5492 (1994).
Munarini, N., "Altered mammary epithelial development, pattern formation and involution in transgenic mice expressing the EphB4 receptor tyrosine kinase," J. Cell. Sci., 115(Pt 1):25-37 (2002).
Nakanuma, Y. et al., "Succinylated Wheat Germ Agglutinin Lectin Binding in Intrahepatic Vessels: A New Histochemical Tool," Arch. Pathol. Lab. Med., 117:809-811 (1993).
Niklason, L.E., et al., "Functional Arteries Grown In Vitro," Science, 284:489-493 (1999).
Niklason, L.E., et al., "Morphologic and Mechanical Characteristics of Engineered Bovine Arteries," J. Vasc. Surg., 33:628-638 (2001).
Nikolova, et al., "Cell-type specific and estrogen dependent expression of the receptor tyrosine kinase EphB4 and its ligand ephrin-B2 during mammary gland morphogenesis," Journal of Cell Science, 111:2741-2751 (1998).
Nomura, A.M., et al., "Prostate cancer: a current perspective," Epidemiol Rev., 13:200-227 (1991).
Noren et al., The EphB4 receptor suppresses breast cancer cell tumorigenicity through an Abl-Crk pathway, Nature Cell Bio. 8:815-825 (2006).
Noren et al., "Interplay Between EphB4 on Tumor Cells and Vascular Ephrin-B2 Regulates Tumor Growth," Proceedings of the National Academy of Sciences of USA, National Academy of Science, 101(15):5583-5588 (2004).
Ogle et al., "The Role of Vascular Smooth Muscle Cell Integrins in the Compaction and Mechanical Strengthening of a Tissue-Engineered Blood Vessel," Tissue Engineering, 5(4):387-402 (1999).
Orioli, D., et al., "Sek4 and Nuk Receptors Cooperate in Guidance of Commissural Axons and in Palate Formation," Embo J., 15(22):6035-6049. (1996).
Pandey et al., "Role of B61, the ligand for the eck receptor tyrosine kinase, in TNF-a-induced angiogenisis" Science, 268:567-569 (1996).
Parangi et al., "Antiangiogenic therapy of transgenic mice impairs de novo tumor growth," Proc. Natl. Acad. Sci. USA, 93:2002-2007 (1996).
Pasquale, E.B., "The Eph family of receptors," Curr. Opin. Cell Biol., 9:608-615 (1997).
Peng et al., "Regulation of Ca2+-activated K+ channels in pulmonary vascular smooth muscle cells: role of nitric oxide," J. Applied Physiol., 81:1264-1272 (1996).
Perrin et al., "Expression, Purification, and Characterization of a Soluble Form of the First Extracellular Domain of the Human Type 1 Corticotropin Releasing Factor Receptor*," The Journal of Biological Chemistry, vol. 276(34), pp. 31528-31534 (2001).
Presta et al., "Humanization of an Anti-Vascular Endothelial Growth Factor Monoclonal Antibody for the Therapy of Solid Tumors and Other Disorders," Cancer Research, 57:4593-4599 (1997).
R&D systems. Recombinant Mouse EphB4/Fc chimera. Nov. 14, 2000. p. 1.
Ramchandran et al., Mettaloprotease-mediated cleavage secretion of pulmonary ACE by vascular endothelial and kidney epithelial cells,: Am. J. Physiology, 271:H744-751 (1996).
Risau, W., "Mechanisms of angiogenesis," Nature, 386:671-674 (1997).
Sakano, S., et al., "Characterization of a ligand for receptor protein-tyrosine kinase HTK expressed in immature hematopoietic cells," Oncogene., 13:813-822 (1996).
Santa Cruz Biotech Inc. datasheet for EphB4(H-200) (undated).
Santa Cruz Biotechnology, Inc., "EphB4 (N-19): sc-7285", retrieved from the Internet: URL:http://www.genetimes.com.cn/support/pdf-ds/7200-7299/sc-7285.pdf (1999).
Santa Cruz, "EphB4 (N-19): sc-7285," Product Catalog of Santa Cruz Biotechnology, Apr. 1999.
Schmucker, D., et al., "Signaling Downstream of Eph Receptors and Ephrin Ligands," Cell, 105:701-704 (2001).

Seffernick et al., "Melamine Deaminase and Atrazine Chlorohydrolase: 98 Percent Identical but Functionally Different", Journal of Bacteriology, vol. 183(8), pp. 2405-2410 (2001).
Shepard, et al., "Monoclonal Antibody Therapy of Human Cancer: Taking the HER2 Protooncogene to the Clinic," Journal of Clinical Immunology, 11(3):117-127 (1991).
Shin, D., et al., "Expression of ephrinB2 identifies a stable genetic difference between arterial and venous vascular smooth muscle as well as endothelial cells, and marks subsets of microvessels at sites of adult neovascularization," Dev. Biol. 230:139-150 (2001).
Simonet, S., et al., "Venous and Arterial Endothelial Cells Respond Differently to Thrombin and its Endogenous Receptor Agonist," European Journal of Pharmacology, 216:135-137 (1992).
Simons, M., et al., "Antisense c-myb Oligonucleotides Inhibit Intimal Arterial Smooth Muscle Cell Accumulation In Vivo," Nature, 359(6390):67-70 (1992).
Sinha, et al., "Expression of EphB4 in head and neck squamous cell carcinoma" Ear, Nose and Throat Journal, 82(11), pp. 866, 869-870 & 887 (2003).
Sinha, U.K., et al., "Expression of EphB4 in head and neck squamous cell carcinoma," ENT J 82:721-723 (2003).
Sola et al., "Transgenic Mice Secreting Coronavirus Neutralizing Antibodies into the Milk", Journal of Virology, vol. 72(5), pp. 3762-3772 (1998).
Staton et al., Current Methods for Assaying Angiogenesis in vitro and in vivo, Int. J. Exp. Path. 85:233-248 (2004).
Stein, E. et al., "Eph receptors discriminate specific ligand oligomers to determine alternative signaling complexes, attachment, and assembly responses," Genes & Development, 12:667-678 (1998).
Stein, E. et al., "Nck Recruitment to Eph Receptor, EphB1/ELK, Couples Ligand Activation to c-Jun Kinase," The Journal of Biological Chemistry, 273(3):1303-1308 (1998).
Steinle, J.J., et al., "Eph B4 receptor signaling mediates endothelial cell migration and proliferation via the phosphatidylinositol 3-kinase pathway," J. Biol. Chem., 277(46):43830-5 (Nov. 15, 2002) (Epub Sep. 13, 2002).
Stephenson, S.A., "Receptor protein tyrosine kinase EphB4 is up-regulated in colon cancer," BMC Mol. Biol., 2:15 (2001).
Sturz, et al., "EphB4 signaling is capable of mediating ephrinB2-induced inhibition of cell migration," Biochemical and Biophysical Research Communications, 313:80-88 (2004).
Sunassee, et al., "Tumour angiogenesis: Hitting cancer where it hurts," Current Biology, 7(5):R282-R285 (1997).
Takai, N., et al., "Expression of receptor tyrosine kinase EphB4 and its ligand ephrin-B2 is associated with malignant potential in endometrial cancer," Oncol Rep., 8:567-573 (2001).
Tallquist, M.D., et al., "Growth Factor Signaling Pathways in Vascular Development," Oncogene, 18(55):7917-7932 (1999).
Tang, X.X., et al., "Coexpression of transcripts encoding EphB receptor protein tyrosine kinases and their ephrin-B ligands in human small cell lung carcinoma," Clin. Cancer Res., 5:455-460 (1999).
The Eph Nomenclature Committee, "Unified Nomenclature for Eph Family Receptors and Their Ligands, the Ephrins," Cell, 90:403-404 (1997).
Thurston et al., "Permeability-related changes revealed at endothelial cell borders in inflamed venules by lectin binding," American Journal of Physiology, 271:H2547-H2562 (1996).
Tsui, L.V., et al., "p27-p16 Fusion Gene Inhibits Angioplasty-Induced Neointimal Hyperplasia and Coronary Artery Occlusion," Circ. Res., 89:323-328 (2001).
Twardowski et al., "Clinical trials of antiangiogenic agents," Current Opinion in Oncology, 9:584-589 (1997).
Van De Wiei et al., "Factors that define the susceptibility of endothelial cells to tumor necrosis factor and lipid A," Immunopharmacology, 23:49-56 (1992).
Vasgene Therapeutics, Inc., "Statement of Grounds of Opposition," In the Matter of European Patent No. 1135153 (EP-B-1135153), (2006).
Vector Laboratories, "Wheat Germ Agglutinin (WGA)," [online; downloaded Jun. 12, 2006].
Von Der Leyen, H.E., et al., "Gene Therapy Inhibiting Neointimal Vascular Lesion: In Vivo Transfer of Endothelial Cell Nitric Oxide Synthase Gene," Proc. Natl. Acad. Sci., 92:1137-1141 (1995).

(56) References Cited

OTHER PUBLICATIONS

Wang et al., "Molecular Distinction and Angiogenic Interactions Between Embryonic Arteries and Veins Revealed by EphrinB2 and Its Receptor EphB4," Circulation: Melvin L. Marcus Young Investigator Award, Abstract 341 (1998).
Wang, H. U. et al., "Eph Family Transmembrane Ligands Can Mediate Repulsive Guidance of Trunk Neural Crest Migration and Motor Axon Outgrowth," Neuron, 18:383-396 (1997).
Wang, H., "Transmembrane Ephrin Ligands in Neural and Vascular Development," DAI, 59(11): 5721 (1999).
Wang, H.U., et al., "Molecular distinction and angiogenic interaction between embryonic arteries and veins revealed by ephrin-B2 and its receptor Eph-B4," Cell 93:741-753 (1998).
Wang, Eph tumour suppression: the dark side of Gleevec, Nat. Cell Biol. 8(8):785-786 (2006).
Waugh, J.M., et al., "Thrombomodulin Overexpression to Limit Neointima Formation," Circulation, 102:332-337 (2000).
Winlaw, "Angiogenesis in the Pathobiology and Treatment of Vascular and Malignant Diseases," Ann. Thorac. Surg., 64:1204-1211 (1997).
Xia et al., "Up-Regulation of EphB4 in Mesothelioma and Its Biological Significance", Clinical Cancer Research, vol. 11(12), pp. 4305-4315 (2005).
Xu et al., Eph-related receptors and their ligands: mediators of contact dependent cell interactions, J. Mol. Med. 75:576-586 (1997).
Xu, et al., "Function of the Eph-related kinase rtk1 in patterning of the zebrafish forebrain," Nature, 381:19-322 (1996).
Yamamoto et al., "Differences in Cellular Responses to Mitogens in Arterial Smooth Muscle Cells Derived From Patients With Moyamoya Disease," Stroke, 29:1188-1193 (1998).
Yancopoulos, G. D. et al., "Vasculogenesis, Angiogenesis, and Growth Factors: Ephrins Enter the Fray at the Border," Cell, 93:661-664 (1998).
Yang et al., "Gene Targets of Antisense Therapies in Breast Cancer," Expert Opin. on Therapeutic Targets, 6(3):375-385, (2002).
Yuan, et al., "Syndecan-1 up-regulated by ephrinB2/EphB4 plays dual roles in inflammatory angiogenesis," Blood, 104(4):1025-1033 (2004).
Zetter, "Angiogenesis and Tumor Metastasis," Annu. Rev. Med, 49:407-424, (1998).
Zhang, X-Q, et al., "Stromal Cells Expressing ephrin-B2 Promote the Growth and Sprouting of Ephrin-B2+ Endothelial Cells," Blood, 98:1028-37 (2001).
Zhou, "The Eph Family Receptor and Ligands," Pharmacol. Ther. ,77(3) 151-181 (1998).
Chrencik at al., "Structural and biophysical characterization of the EphB4/EphrinB2 protein-protein interaction and receptor specificity," J. Biol. Chem. 281:38:28185-92 (2006).
Gale et al., "Eph receptors and ligands comprise two major specificity subclasses and are reciprocally compartmentalized during embryogenesis," Neuron 17:9-19 (1996).

* cited by examiner

Figure 1: human EphB4 receptor precursor sequence and structure.

```
  1 melrvllcwa slaaaleetl lntkletadl kwvtfpqvdg qweelsglde eqhsvrtyev
 61 cdvqrapgqa hwlrtgwvpr rgavhvyatl rftmleclsl pragrscket ftvfyyesda
121 dtataltpaw menpyikvdt vaaehltrkr pgaeatgkvn vktlrlgpls kagfylafqd
181 qgacmallsl hlfykkcaql tvnitrfpet vprelvvpva gscvvdavpa pgpspslycr
241 edgqwaeqpv tgcscapgfe aaegntkcra caqgtfkpls gegscqpcpa nshsntigsa
301 vcqcrvgyfr artdprgapc ttppsaprsv vsrlngsslh lewsaplesg gredltyalr
361 crecrpggsc apcggdltfd pgprdlvepw vvvrglrpdf tytfevtaln gvsslatgpv
421 pfepvnvttd revppavsdi rvtrsspssl slawavprap sgavldyevk yhekgaegps
481 svrflktsen raelrglkrg asylvqvrar seagygpfgq ehhsqtqlde segwreqlal
541 iagtavvgvv lvlvvivvav lclrkqsngr eaeysdkhgq ylighgtkvy idpftyedpn
601 eavrefakei dvsyvkieev igagefgevc rgrlkapgkk escvaiktlk ggyterqrre
661 flseasimgq fehpniirle gvvtnsmpvm iltefmenga ldsflrlndg qftviqlvgm
721 lrglasgmry laemsyvhrd laarnilvns nlvckvsdfg lsrfleenss dptytsslgg
781 kipirwtape aiafrkftsa sdawsygivm wevmsfgerp ywdmsnqdvi naieqdyrlp
841 pppdcptslh qlmldcwqkd rnarprfpqv vsaldkmirn paslkivare nggashplld
901 qrqphysafg svgewlraik mgryeesfaa agfgsfelvs qisaedllri gvtlaghqkk
961 ilasvqhmks qakpgtpggt ggpapqy
```

Figure 2: EphB4 mRNA

```
   1 ctcggcccgg cggcgcgagc agagccactc cagggagggg gggagaccgc gagcggccgg
  61 ctcagccccc gccacccggg gcgggacccc gaggcccgg agggacccca actccagcca
 121 cgtcttgctg cgcgcccgcc cggcgcggcc actgccagca cgctcccggc ccgccgcccg
 181 cgcgcgcggc acagacgcgg ggccacactt ggcgccgccg cccggtgccc cgcacgctcg
 241 catgggcccg cgctgagggc cccgacgagg agtcccgcgc ggagtatcgg cgtccacccg
 301 cccagggaga gtcagacctg ggggggcgag ggccccccaa actcagttcg gatcctaccc
 361 gagtgaggcg gcgccatgga gctccgggtg ctgctctgct gggcttcgtt ggccgcagct
 421 ttggaagaga ccctgctgaa cacaaaattg gaaactgctg atctgaagtg ggtgacattc
 481 cctcaggtgg acgggcagtg ggaggaactg agcggcctgg atgaggaaca gcacagcgtg
 541 cgcacctacg aagtgtgtga cgtgcagcgt gcccccgggcc aggcccactg gcttcgcaca
 601 ggttgggtcc cacggcgggg cgccgtccac gtgtacgcca cgctgcgctt caccatgctc
 661 gagtgcctgt ccctgcctcg ggctgggcgc tcctgcaagg agaccttcac cgtcttctac
 721 tatgagagcg atgcggacac ggccacggcc ctcacgccag cctggatgga gaaccctac
 781 atcaaggtgg acacggtggc cgcggagcat ctcacccgga agcgcctgg ggccgaggcc
 841 accgggaagg tgaatgtcaa gacgctgcgt ctggaccgc tcagcaaggc tggcttctac
 901 ctggccttcc aggaccaggg tgcctgcatg gccctgctat ccctgcacct cttctacaaa
 961 aagtgcgccc agctgactgt gaacctgact cgattccgg agactgtgcc tgggagctg
1021 gttgtgcccg tggccggtag ctgcgtggtg gatgccgtcc ccgcccctgg ccccagcccc
1081 agcctctact gccgtgagga tggccagtgg gccgaacagc cggtcacggg ctgcagctgt
1141 gctccggggt tcgaggcagc tgagggaac accaagtgcc gagcctgtgc cagggcacc
1201 ttcaagcccc tgtcaggaga agggtcctgc cagccatgcc cagccaatag ccactctaac
1261 accattggat cagccgtctg ccagtgccgc gtcgggtact tccgggcacg cacagacccc
1321 cggggtgcac cctgcaccac ccctccttcg gctccgcgga gcgtggtttc ccgcctgaac
1381 ggctcctccc tgcacctgga atggagtgcc cccctggagt ctggtggccg agaggacctc
1441 acctacgccc tccgctgccg ggagtgccga cccggaggct cctgtgcgcc ctgcggggga
1501 gacctgactt tgacccccgg cccccgggac ctggtggagc cctggtggt ggttcgaggg
1561 ctacgtcctg acttcaccta tacctttgag gtcactgcat tgaacgggt atcctcctta
1621 gccacgggtg ccgtccatt tgaacctgtc aatgtcacca ctgaccgaga ggtacctcct
1681 gcagtgtctg acatccgggt gacgcggtcc tcacccagca gcttgagcct ggcctgggct
1741 gttccccggg cacccagtgg ggctgtgctg gactacgagg tcaaatacca tgagaagggc
1801 gccgagggtc ccagcagcgt gcggttcctg aagacgtcag aaaaccgggc agagctgcgg
1861 gggctgaagc ggggagccag ctacctggtg caggtacggg cgcgctctga ggccggctac
1921 gggcccttcg gccaggaaca tcacagccag acccaactgg atgagagcga gggctggcgg
1981 gagcagctgg ccctgattgc gggcacggca gtcgtgggtg tggtcctggt cctggtggtc
2041 attgtggtcg cagttctctg cctcaggaag cagagcaatg ggagagaagc agaatattcg
2101 gacaaacacg gacagtatct catcggacat ggtactaagg tctacatcga ccccttcact
2161 tatgaagacc ctaatgaggc tgtgagggaa tttgcaaaag agatcgatgt ctcctacgtc
2221 aagattgaag aggtgattgg tgcaggtgag tttggcgagg tgtgccgggg gcggctcaag
2281 gccccaggga gaaggagag ctgtgtggca atcaagaccc tgaagggtgg ctacacggag
2341 cggcagcggc gtgagttct gagcgaggcc tccatcatgg gccagttcga gcacccaat
2401 atcatccgct tggagggcgt ggtcaccaac agcatgcccg tcatgattct cacagagttc
2461 atggagaacg cgccctgga ctccttcctg cggctaaacg acggacagtt cacagtcatc
2521 cagctcgtgg gcatgctgcg gggcatcgcc tcgggcatgc ggtaccttgc cgagatgagc
2581 tacgtccacc gagacctggc tgctcgcaac atcctagtca acagcaacct cgtctgcaaa
2641 gtgtctgact ttggcctttc ccgattcctg gaggagaact cttccgatcc cacctacacg
2701 agctccctgg gaggaaagat tccatccga tggactgccc cggaggccat tgccttccgg
2761 aagttcactt ccgccagtga tgcctggagt tacgggattg tgatgtggga ggtgatgtca
2821 tttgggagag gccgtactg ggacatgagc aatcaggacg tgatcaatgc cattgaacag
2881 gactacggc tgcccccgcc ccagactgt cccacctcc tccaccagct catgctggac
2941 tgttggcaga agaccggaa tgccggcccc cgcttccccc aggtggtcag cgccctggac
3001 aagatgatcc ggaaccccgc cagcctcaaa atcgtggccc gggagaatgg cggggcctca
3061 caccctctcc tggaccagcc gcagcctcac tactcagctt ttggctctgt gggcgagtgg
3121 cttcggggcca tcaaatggg aagatacgaa gaaagttctcg cagccgctgg cttcggctcc
3181 ttcgagctgg tcagccagat ctctgctgag gacctgctcc gaatcggagt cactctggcg
3241 ggacaccaga agaaaatctt ggccagtgtc cagcacatga gtccaggc caagccggga
3301 acccgggtg ggacaggagg accggccccg cagtactgac ctgcaggaac tcccaccc
```

```
3361 agggacaccg cctcccatt ttccggggca gagtgggac tcacagaggc ccccagccct
3421 gtgcccgct ggattgcact ttgagcccgt ggggtgagga gttggcaatt tggagagaca
3481 ggatttgggg gttctgccat aataggaggg gaaaatcacc ccccagccac ctcggggaac
3541 tccagaccaa gggtgagggc gcctttccct caggactggg tgtgaccaga ggaaaaggaa
3601 gtgcccaaca tctcccagcc tccccaggtg ccccctcac cttgatgggt gcgttcccgc
3661 agaccaaaga gagtgtgact ccctgccag ctccagagtg gggggctgt cccaggggc
3721 aagaaggggt gtcagggccc agtgacaaaa tcattggggt ttgtagtccc aacttgctgc
3781 tgtcaccacc aaactcaatc atttttttcc cttgtaaatg ccctccccc agctgctgcc
3841 ttcatattga aggtttttga gttttgtttt tggtcttaat ttttctcccc gttcccttttt
3901 tgtttcttcg ttttgttttt ctaccgtcct tgtcataact ttgtgttgga gggaacctgt
3961 ttcactatgg cctcctttgc ccaagttgaa acagggccc atcatcatgt ctgtttccag
4021 aacagtgcct tggtcatccc acatccccgg acccgcctg ggaccccaa gctgtgtcct
4081 atgaaggggt gtgggtgag gtagtgaaaa gggcggtagt tggtggtgga acccagaaac
4141 ggacgccggt gcttggaggg gttcttaaat tatatttaaa aaagtaactt tttgtataaa
4201 taaaagaaaa tgggacgtgt cccagctcca ggggt
```

Fig. 2, cont.

Figure 3: Amino acid sequence of the B4ECv3 protein (EphB4 extracellular domain)

```
MELRVLLCWASLAAALEETLLNTKLETADLKWVTFPQVDGQWEELSG
LDEEQHSVRTYEVCEVQRAPGQAHWLRTGWVPRRGAVHVYATLRFTM
LECLSLPRAGRSCKETFTVFYYESDADTATALTPAWMENPYIKVDTV
AAEHLTRKRPGAEATGKVNVKTLRLGPLSKAGFYLAFQDQGACMALL
SLHLFYKKCAQLTVNLTRFPETVPRELVVPVAGSCVVDAVPAPGPSP
SLYCREDGQWAEQPVTGCSCAPGFEAAEGNTKCRACAQGTFKPLSGE
GSCQPCPANSHSNTIGSAVCQCRVGYFRARTDPRGAPCTTPPSAPRS
VVSRLNGSSLHLEWSAPLESGGREDLTYALRCRECRPGGSCAPCGGD
LTFDPGPRDLVEPWVVVRGLRPDFTYTFEVTALNGVSSLATGPVPFE
PVNVTTDREVPPAVSDIRVTRSSPSSLSLAWAVPRAPSGAWLDYEVK
YHEKGAEGPSSVRFLKTSENRAELRGLKRGASYLVQVRARSEAGYGP
FGQEHHSQTQLDESEGWREQGSKRAILQIEGKPIPNPLLGLDSTRTG
HHHHHH
```

Figure 4: Amino acid sequence of the B4ECv3NT protein (EphB4 extracellular domain)

```
MELRVLLCWASLAAALEETLLNTKLETADLKWVTFPQVDGQWEELSG
LDEEQHSVRTYEVCEVQRAPGQAHWLRTGWVPRRGAVHVYATLRFTM
LECLSLPRAGRSCKETFTVFYYESDADTATALTPAWMENPYIKVDTV
AAEHLTRKRPGAEATGKVNVKTLRLGPLSKAGFYLAFQDQGACMALL
SLHLFYKKCAQLTVNLTRFPETVPRELVVPVAGSCVVDAVPAPGPSP
SLYCREDGQWAEQPVTGCSCAPGFEAAEGNTKCRACAQGTFKPLSGE
GSCQPCPANSHSNTIGSAVCQCRVGYFRARTDPRGAPCTTPPSAPRS
VVSRLNGSSLHLEWSAPLESGGREDLTYALRCRECRPGGSCAPCGGD
LTFDPGPRDLVEPWVVVRGLRPDFTYTFEVTALNGVSSLATGPVPFE
PVNVTTDREVPPAVSDIRVTRSSPSSLSLAWAVPRAPSGAWLDYEVK
YHEKGAEGPSSVRFLKTSENRAELRGLKRGASYLVQVRARSEAGYGP
FGQEHHSQTQLDESEGWREQGSKRAILQISSTVAAARV
```

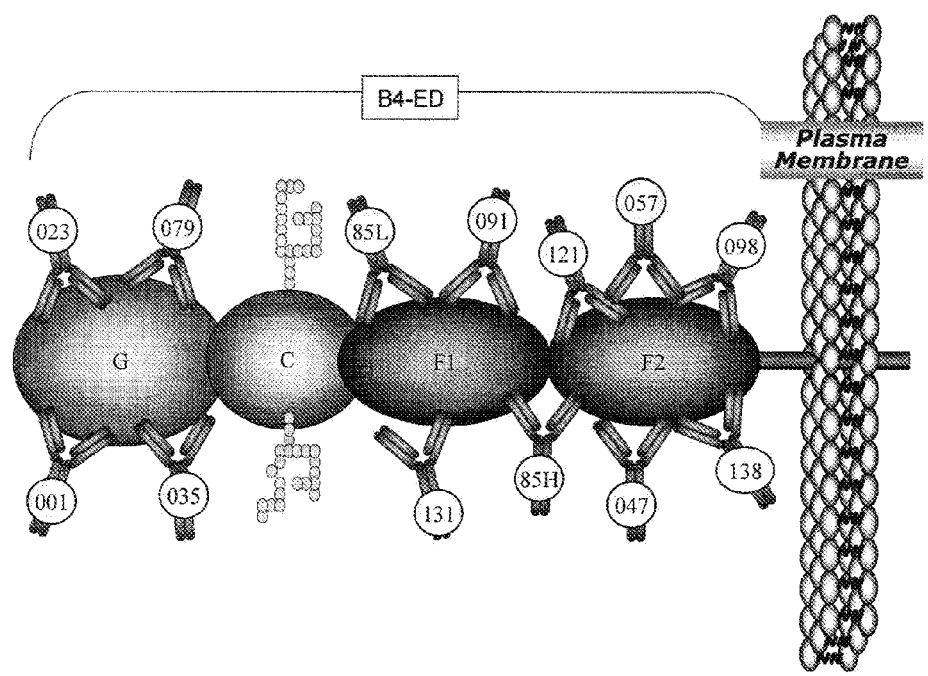
Figure 5: Summary of EphB4 Topology and Antibody Binding Sites

Mouse Corneal Micropocket Assay with B4 AB's

Figure 9: SCC15/MG xenograft tumor regression
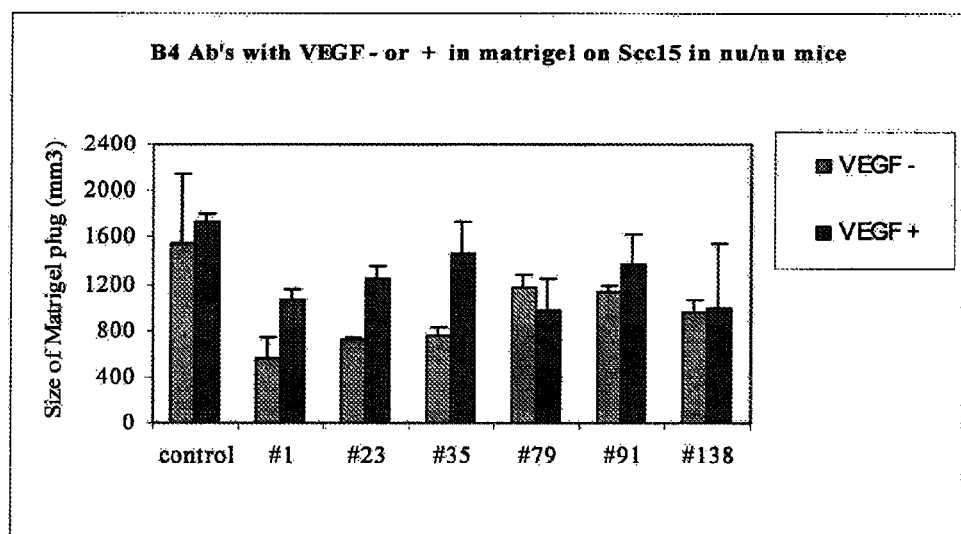

Figure 10: Effect of B4 antibodies on SCC15 Tumor histology
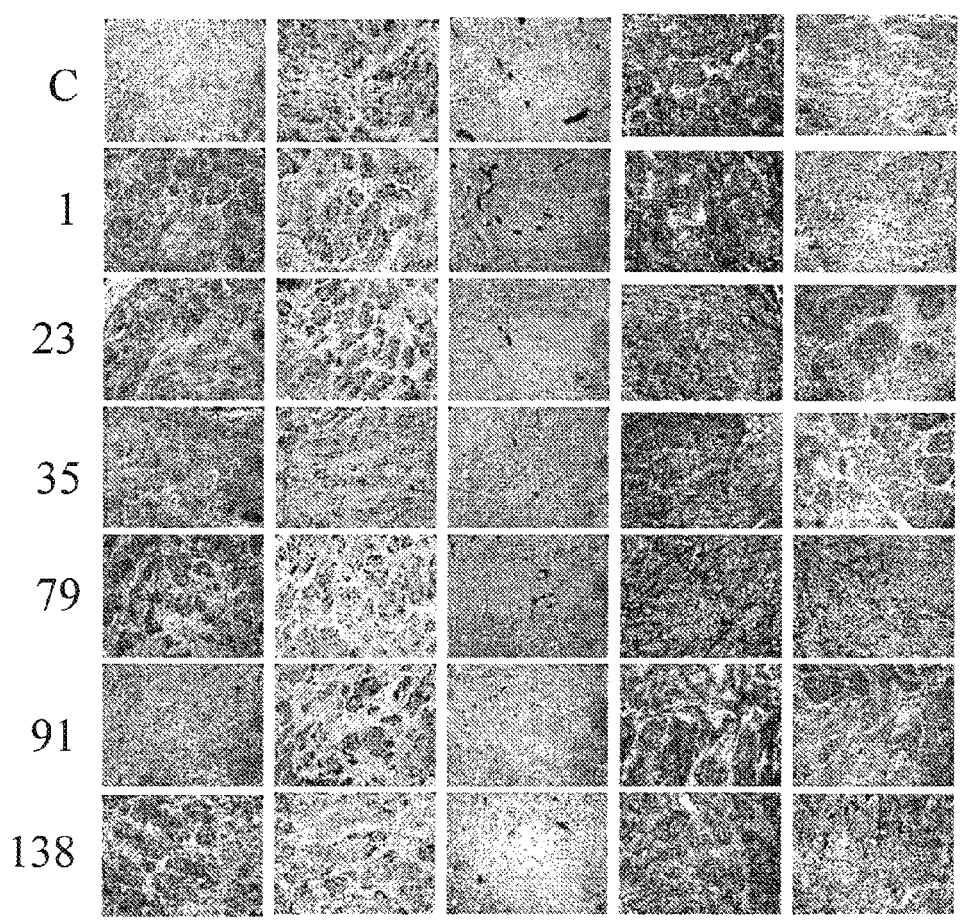

Figure 11: SCC15/IP,SC B4 Ab treated xenograft tumor regression
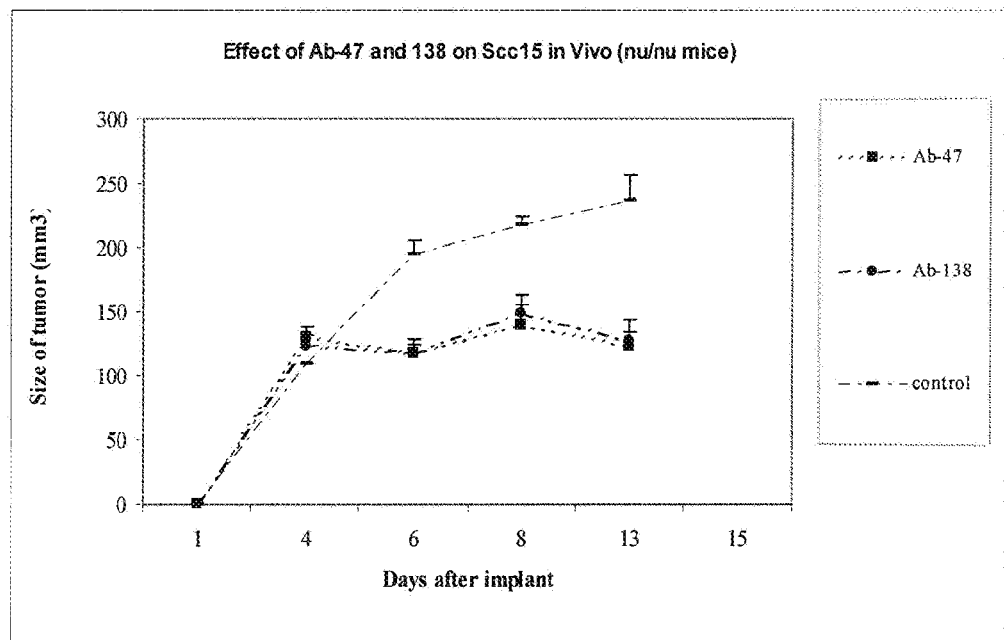
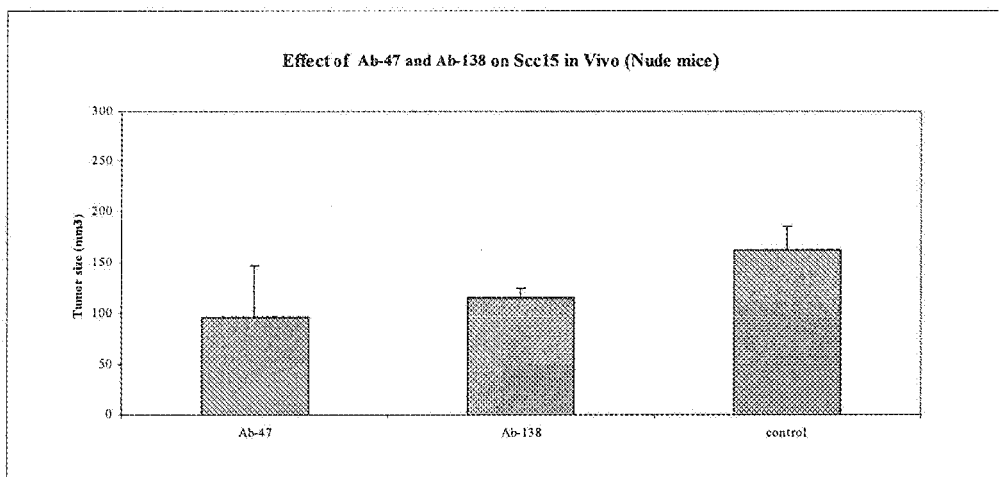

SEQUENCE LISTING

```
<160> NUMBER OF SEQ ID NOS: 4

<210> SEQ ID NO 1
<211> LENGTH: 987
<212> TYPE: PRT
<213> ORGANISM: Homo sapiens

<400> SEQUENCE: 1

Met Glu Leu Arg Val Leu Leu Cys Trp Ala Ser Leu Ala Ala Ala Leu
 1               5                  10                  15

Glu Glu Thr Leu Leu Asn Thr Lys Leu Glu Thr Ala Asp Leu Lys Trp
             20                  25                  30

Val Thr Phe Pro Gln Val Asp Gly Gln Trp Glu Glu Leu Ser Gly Leu
         35                  40                  45

Asp Glu Glu Gln His Ser Val Arg Thr Tyr Glu Val Cys Asp Val Gln
     50                  55                  60

Arg Ala Pro Gly Gln Ala His Trp Leu Arg Thr Gly Trp Val Pro Arg
 65                  70                  75                  80

Arg Gly Ala Val His Val Tyr Ala Thr Leu Arg Phe Thr Met Leu Glu
                 85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335
```

-continued

```
Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Val
    450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln Leu Ala Leu Ile Ala Gly Thr
    530                 535                 540

Ala Val Val Gly Val Val Leu Val Leu Val Val Ile Val Val Ala Val
545                 550                 555                 560

Leu Cys Leu Arg Lys Gln Ser Asn Gly Arg Glu Ala Glu Tyr Ser Asp
                565                 570                 575

Lys His Gly Gln Tyr Leu Ile Gly His Gly Thr Lys Val Tyr Ile Asp
            580                 585                 590

Pro Phe Thr Tyr Glu Asp Pro Asn Glu Ala Val Arg Glu Phe Ala Lys
        595                 600                 605

Glu Ile Asp Val Ser Tyr Val Lys Ile Glu Glu Val Ile Gly Ala Gly
    610                 615                 620

Glu Phe Gly Glu Val Cys Arg Gly Arg Leu Lys Ala Pro Gly Lys Lys
625                 630                 635                 640

Glu Ser Cys Val Ala Ile Lys Thr Leu Lys Gly Gly Tyr Thr Glu Arg
                645                 650                 655

Gln Arg Arg Glu Phe Leu Ser Glu Ala Ser Ile Met Gly Gln Phe Glu
            660                 665                 670

His Pro Asn Ile Ile Arg Leu Glu Gly Val Val Thr Asn Ser Met Pro
        675                 680                 685

Val Met Ile Leu Thr Glu Phe Met Glu Asn Gly Ala Leu Asp Ser Phe
    690                 695                 700

Leu Arg Leu Asn Asp Gly Gln Phe Thr Val Ile Gln Leu Val Gly Met
705                 710                 715                 720

Leu Arg Gly Ile Ala Ser Gly Met Arg Tyr Leu Ala Glu Met Ser Tyr
                725                 730                 735

Val His Arg Asp Leu Ala Ala Arg Asn Ile Leu Val Asn Ser Asn Leu
            740                 745                 750

Val Cys Lys Val Ser Asp Phe Gly Leu Ser Arg Phe Leu Glu Glu Asn
```

```
                    755                 760                 765
Ser Ser Asp Pro Thr Tyr Thr Ser Ser Leu Gly Gly Lys Ile Pro Ile
    770                 775                 780

Arg Trp Thr Ala Pro Glu Ala Ile Ala Phe Arg Lys Phe Thr Ser Ala
785                 790                 795                 800

Ser Asp Ala Trp Ser Tyr Gly Ile Val Met Trp Glu Val Met Ser Phe
                805                 810                 815

Gly Glu Arg Pro Tyr Trp Asp Met Ser Asn Gln Asp Val Ile Asn Ala
            820                 825                 830

Ile Glu Gln Asp Tyr Arg Leu Pro Pro Pro Asp Cys Pro Thr Ser
        835                 840                 845

Leu His Gln Leu Met Leu Asp Cys Trp Gln Lys Asp Arg Asn Ala Arg
    850                 855                 860

Pro Arg Phe Pro Gln Val Val Ser Ala Leu Asp Lys Met Ile Arg Asn
865                 870                 875                 880

Pro Ala Ser Leu Lys Ile Val Ala Arg Glu Asn Gly Gly Ala Ser His
                885                 890                 895

Pro Leu Leu Asp Gln Arg Gln Pro His Tyr Ser Ala Phe Gly Ser Val
            900                 905                 910

Gly Glu Trp Leu Arg Ala Ile Lys Met Gly Arg Tyr Glu Glu Ser Phe
        915                 920                 925

Ala Ala Ala Gly Phe Gly Ser Phe Glu Leu Val Ser Gln Ile Ser Ala
    930                 935                 940

Glu Asp Leu Leu Arg Ile Gly Val Thr Leu Ala Gly His Gln Lys Lys
945                 950                 955                 960

Ile Leu Ala Ser Val Gln His Met Lys Ser Gln Ala Lys Pro Gly Thr
                965                 970                 975

Pro Gly Gly Thr Gly Gly Pro Ala Pro Gln Tyr
            980                 985

<210> SEQ ID NO 2
<211> LENGTH: 4235
<212> TYPE: DNA
<213> ORGANISM: Homo sapiens

<400> SEQUENCE: 2
ctcggcccgg cggcgcgagc agagccactc cagggagggg gggagaccgc gagcggccgg    60
ctcagccccc gccacccggg gcgggacccc gaggccccgg agggacccca actccagcca   120
cgtcttgctg cgcgcccgcc cggcgcggcc actgccagca cgctccgggc ccgccgcccg   180
cgcgcgcggc acagacgcgg ggccacactt ggcgccgccg cccggtgccc cgcacgctcg   240
catgggcccg cgctgagggc cccgacgagg agtcccgcgc ggagtatcgg cgtccacccg   300
cccagggaga gtcagacctg gggggcgag ggccccccaa actcagttcg atcctaccc    360 gagtgaggcg cgccatggca gctccgggtg ctgctctgct gggcttcgtt ggccgcagct   420
ttggaagaga ccctgctgaa cacaaaattg gaaactgctg atctgaagtg ggtgacattc   480
cctcaggtgg acgggcagtg ggaggaactg agcggcctgg atgaggaaca gcacagcgtg   540
cgcacctacg aagtgtgtga cgtgcagcgt gccccgggcc aggccactg gcttcgcaca    600 ggttgggtcc cacggcgggg cgccgtccac gtgtacgcca cgctgcgctt caccatgctc   660
gagtgcctgt ccctgcctcg ggctgggcgc tcctgcaagg agaccttcac cgtcttctac   720
tatgagagcg atgcggacac ggccacggcc ctcacgccag cctggatgga gaaccccta   780 atcaaggtgg acacggtggc cgcggagcat ctcacccgga agcgccctgg ggccgaggcc   840
```

```
accgggaagg tgaatgtcaa gacgctgcgt ctgggaccgc tcagcaaggc tggcttctac      900
ctggccttcc aggaccaggg tgcctgcatg ccctgctat ccctgcacct cttctacaaa       960
aagtgcgccc agctgactgt gaacctgact cgattcccgg agactgtgcc tcgggagctg     1020
gttgtgcccg tggccggtag ctgcgtggtg gatgccgtcc ccgccctgg ccccagcccc      1080 agcctctact gccgtgagga tggccagtgg gccgaacagc cggtcacggg ctgcagctgt     1140
gctccggggt tcgaggcagc tgaggggaac accaagtgcc gagcctgtgc cagggcacc     1200 ttcaagcccc tgtcaggaga agggtcctgc cagccatgcc cagccaatag ccactctaac     1260
accattggat cagccgtctg ccagtgccgc gtcgggtact tccgggcacg cacagacccc     1320
cggggtgcac cctgcaccac ccctccttcg gctccgcgga gcgtggtttc ccgcctgaac     1380
ggctcctccc tgcacctgga atggagtgcc cccctggagt ctggtggccg agaggacctc     1440
acctacgccc tccgctgccg ggagtgccga cccggaggct cctgtgcgcc ctgcggggga     1500
gacctgactt tgaccccgg ccccgggac ctggtggagc cctgggtggt ggttcgaggg       1560
ctacgtcctg acttcaccta tacctttgag gtcactgcat tgaacggggt atcctcctta    1620
gccacggggc ccgtcccatt tgagcctgtc aatgtcacca ctgaccgaga ggtacctcct    1680
gcagtgtctg acatccgggt gacgcggtcc tcacccagca gcttgagcct ggcctgggct    1740
gttccccggg cacccagtgg ggctgtgctg gactacgagg tcaaatacca tgagaagggc    1800
gccgagggtc ccagcagcgt gcggttcctg aagacgtcag aaaaccgggc agagctgcgg    1860
gggctgaagc ggggagccag ctacctggtg caggtacggg cgcgctctga ggccggctac    1920
gggcccttcg gccaggaaca tcacagccag acccaactgg atgagagcga gggctggcgg    1980
gagcagctgg ccctgattgc gggcacggca gtcgtgggtg tggtcctggt cctggtggtc    2040
attgtggtcg cagttctctg cctcaggaag cagagcaatg ggagagaagc agaatattcg    2100
gacaaacacg gacagtatct catcggacat ggtactaagg tctacatcga ccccttcact    2160
tatgaagacc ctaatgaggc tgtgagggaa tttgcaaaag atcgatgt ctcctacgtc      2220 aagattgaag aggtgattgg tgcaggtgag tttggcgagg tgtgccgggg gcggctcaag    2280
gccccaggga agaaggagag ctgtgtggca atcaagaccc tgaagggtgg ctacacggag    2340
cggcagcggc gtgagtttct gagcgaggcc tccatcatgg ccagttcga gcaccccaat     2400 atcatccgcc tggagggcgt ggtcaccaac agcatgccg tcatgattct cacagagttc    2460
atggagaacg gcgccctgga ctccttcctg cggctaaacg acggacagtt cacagtcatc    2520
cagctcgtgg gcatgctgcg gggcatcgcc tcgggcatgc ggtaccttgc cgagatgagc    2580
tacgtccacc gagacctggc tgctcgcaac atcctagtca acagcaacct cgtctgcaaa    2640
gtgtctgact ttggcctttc ccgattcctg gaggagaact cttccgatcc cacctacacg    2700
agctccctgg aggaaagat tcccatccga tggactgccc cggaggccat tgccttccgg    2760
aagttcactt ccgccagtga tgcctggagt tacgggattg tgatgtggga ggtgatgtca    2820 tttgggggaga ggccgtactg ggacatgagc aatcaggacg tgatcaatgc cattgaacag    2880
gactaccggc tgccccgcc cccagactgt cccacctccc tccaccagct catgctggac    2940
tgttggcaga aagaccggaa tgcccggccc cgcttccccc aggtggtcag cgccctggac    3000
aagatgatcc ggaacccgc cagcctcaaa atcgtggccc gggagaatgg cggggcctca    3060
caccctctcc tggaccagcg gcagcctcac tactcagctt ttggctctgt gggcgagtgg    3120
cttcgggcca tcaaaatggg aagatacgaa gaaagtttcg cagccgctgg ctttggctcc    3180
```

```
ttcgagctgg tcagccagat ctctgctgag gacctgctcc gaatcggagt cactctggcg    3240
ggacaccaga agaaaatctt ggccagtgtc cagcacatga agtcccaggc caagccggga    3300
accccgggtg ggacaggagg accggccccg cagtactgac ctgcaggaac tccccacccc    3360
agggacaccg cctccccatt ttccggggca gagtggggac tcacagaggc ccccagccct    3420
gtgccccgct ggattgcact tgagcccgt ggggtgagga gttggcaatt tggagagaca     3480
ggatttgggg gttctgccat aataggaggg gaaaatcacc ccccagccac ctcggggaac    3540
tccagaccaa gggtgagggc gccttttcct caggactggg tgtgaccaga ggaaaaggaa    3600
gtgcccaaca tctcccagcc tcccaggtg ccccctcac cttgatgggg gcgttcccgc      3660
agaccaaaga gagtgtgact cccttgccag ctccagagtg ggggggctgt cccaggggc     3720 aagaaggggt gtcagggccc agtgacaaaa tcattggggt ttgtagtccc aacttgctgc    3780
tgtcaccacc aaactcaatc attttttttcc cttgtaaatg cccctccccc agctgctgcc   3840
ttcatattga aggttttttga gttttgtttt tggtcttaat ttttctcccc gttccctttt   3900
tgtttcttcg ttttgttttt ctaccgtcct tgtcataact ttgtgttgga gggaacctgt    3960
ttcactatgg cctcctttgc ccaagttgaa acaggggccc atcatcatgt ctgtttccag    4020
aacagtgcct tggtcatccc acatccccgg accccgcctg ggaccccaaa gctgtgtcct   4080
atgaaggggt gtggggtgag gtagtgaaaa gggcggtagt tggtggtgga acccagaaac    4140
ggacgccggt gcttggaggg gttcttaaat tatatttaaa aaagtaactt tttgtataaa    4200
taaaagaaaa tgggacgtgt cccagctcca ggggt                              4235
```

<210> SEQ ID NO 3
<211> LENGTH: 570
<212> TYPE: PRT
<213> ORGANISM: Homo sapiens

<400> SEQUENCE: 3

```
Met Glu Leu Arg Val Leu Leu Cys Trp Ala Ser Leu Ala Ala Ala Leu
 1               5                  10                  15

Glu Glu Thr Leu Leu Asn Thr Lys Leu Glu Thr Ala Asp Leu Lys Trp
             20                  25                  30

Val Thr Phe Pro Gln Val Asp Gly Gln Trp Glu Glu Leu Ser Gly Leu
         35                  40                  45

Asp Glu Glu Gln His Ser Val Arg Thr Tyr Glu Val Cys Glu Val Gln
     50                  55                  60

Arg Ala Pro Gly Gln Ala His Trp Leu Arg Thr Gly Trp Val Pro Arg
 65                  70                  75                  80

Arg Gly Ala Val His Val Tyr Ala Thr Leu Arg Phe Thr Met Leu Glu
                 85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190
```

```
Phe Tyr Lys Lys Cys Ala Gln Leu Thr Val Asn Leu Thr Arg Phe Pro
        195                 200                 205

Glu Thr Val Pro Arg Glu Leu Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Trp
    450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln Gly Ser Lys Arg Ala Ile Leu
    530                 535                 540

Gln Ile Glu Gly Lys Pro Ile Pro Asn Pro Leu Leu Gly Leu Asp Ser
545                 550                 555                 560

Thr Arg Thr Gly His His His His
                565                 570

<210> SEQ ID NO 4
<211> LENGTH: 555
<212> TYPE: PRT
<213> ORGANISM: Homo sapiens
```

```
<400> SEQUENCE: 4

Met Glu Leu Arg Val Leu Leu Cys Trp Ala Ser Leu Ala Ala Ala Leu
 1               5                   10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Glu Val Gln
    50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415
```

-continued

```
Thr Gly Pro Val Pro Phe Glu Pro Val Asn Val Thr Thr Asp Arg Glu
            420             425             430
Val Pro Pro Ala Val Ser Asp Ile Arg Val Thr Arg Ser Ser Pro Ser
        435             440             445
Ser Leu Ser Leu Ala Trp Ala Val Pro Arg Ala Pro Ser Gly Ala Trp
    450             455             460
Leu Asp Tyr Glu Val Lys Tyr His Glu Lys Gly Ala Glu Gly Pro Ser
465             470             475             480
Ser Val Arg Phe Leu Lys Thr Ser Glu Asn Arg Ala Glu Leu Arg Gly
                485             490             495
Leu Lys Arg Gly Ala Ser Tyr Leu Val Gln Val Arg Ala Arg Ser Glu
            500             505             510
Ala Gly Tyr Gly Pro Phe Gly Gln Glu His His Ser Gln Thr Gln Leu
        515             520             525
Asp Glu Ser Glu Gly Trp Arg Glu Gln Gly Ser Lys Arg Ala Ile Leu
    530             535             540
Gln Ile Ser Ser Thr Val Ala Ala Arg Val
545             550             555
```

POLYPEPTIDE COMPOUNDS FOR INHIBITING ANGIOGENESIS AND TUMOR GROWTH

RELATED APPLICATIONS

This application is a continuation of U.S. application Ser. No. 10/592,284 filed Nov. 7, 2007, now U.S. Pat. No. 7,977,463, issued Jul. 12, 2011, which is a national stage filing under 35 U.S.C. 371 of International Application PCT/US2005/008280 filed Mar. 11, 2005, which claims the benefit of priority of U.S. Provisional Application No. 60/612,908 filed Sep. 23, 2004, U.S. application Ser. No. 10/949,720 filed Sep. 23, 2004, now U.S. Pat. No. 7,381,410 issued Jun. 3, 2008, and U.S. application Ser. No. 10/800,350 filed Mar. 12, 2004, now U.S. Pat. No. 7,862,816 issued Jan. 4, 2011. The entire teachings of the referenced applications are incorporated herein by reference in their entireties.

BACKGROUND OF THE INVENTION

EphB4, sometimes referred to as Ephrin Receptor B4 or Hepatoma Transmembrane Kinase (HTK), belongs to a family of transmembrane receptor protein-tyrosine kinases. EphB4 has an extracellular domain composed of the ligand-binding domain (also referred to as globular domain), a cysteine-rich domain, and a pair of fibronectin type III repeats (e.g., see FIG. 5). The cytoplasmic domain consists of a juxtamembrane region containing two conserved tyrosine residues; a protein tyrosine kinase domain; a sterile α-motif (SAM) and a PDZ-domain binding motif. EphB4 interacts with the membrane-bound ligand Ephrin B2 (Sakano, S. et al Oncogene. 1996 Aug. 15; 13(4):813-22; Brambilla R. et al EMBO J. 1995 Jul. 3; 14(13):3116-26). EphB4, like other members of the Eph family, is activated by binding of clustered, membrane-attached ephrin ligands (Davis S et al, Science. 1994 Nov. 4; 266(5186):816-9), indicating that contact between cells expressing the receptor and cells expressing the ligand is required for the Eph receptor activation. Upon ligand binding, an EphB4 receptor dimerizes and autophosphorylates the juxtamembrane tyrosine residues to acquire full activation. It has generally been thought that when an EphB4-expressing cell encounters an EphrinB2-expressing cell, the EphB4-EphrinB2 interaction and aggregation triggers signaling in both cells.

EphB4-EphrinB2 signaling has been implicated in angiogenesis (Wang et al. Cell. 1998 May 29; 93(5):741-53; Gerety et al. Mol Cell. 1999 September; 4(3):403-14). Angiogenesis, the development of new blood vessels from the endothelium of a preexisting vasculature, is a critical process in the growth, progression, and metastasis of solid tumors within the host. During physiologically normal angiogenesis, the autocrine, paracrine, and amphicrine interactions of the vascular endothelium with its surrounding stromal components are tightly regulated both spatially and temporally. Additionally, the levels and activities of proangiogenic and angiostatic cytokines and growth factors are maintained in balance. In contrast, the pathological angiogenesis necessary for active tumor growth is sustained and persistent, representing a dysregulation of the normal angiogenic system. Solid and hematopoietic tumor types are particularly associated with a high level of abnormal angiogenesis.

It is generally thought that the development of a tumor consists of sequential, and interrelated steps that lead to the generation of an autonomous clone with aggressive growth potential. These steps include sustained growth and unlimited self-renewal. Cell populations in a tumor are generally characterized by growth signal self-sufficiency, decreased sensitivity to growth suppressive signals, and resistance to apoptosis. Genetic or cytogenetic events that initiate aberrant growth sustain cells in a prolonged "ready" state by preventing apoptosis.

It is a goal of the present disclosure to provide agents and therapeutic treatments for inhibiting angiogenesis and tumor growth.

SUMMARY OF THE INVENTION

In certain aspects, the disclosure provides polypeptide agents that inhibit EphB4 mediated functions, including antibodies and antigen binding portions thereof that bind to and affect EphB4 in particular ways. As demonstrated herein, EphB4 and EphrinB2 participate in various disease states, including cancers and diseases related to unwanted or excessive angiogenesis. Accordingly, certain polypeptide agents disclosed herein may be used to treat such diseases. In further aspects, the disclosure relates to the discovery that EphB4 and/or EphrinB2 are expressed, often at high levels, in a variety of tumors. Therefore, polypeptide agents that downregulate EphB4 or EphrinB2 function may affect tumors by a direct effect on the tumor cells as well as an indirect effect on the angiogenic processes recruited by the tumor. In certain embodiments, the disclosure provides the identity of tumor types particularly suited to treatment with an agent that downregulates EphB4 or EphrinB2 function.

In certain aspects, the disclosure provides an isolated antibody or antigen binding portion thereof that binds to an epitope situated in the extracellular portion of EphB4 and inhibits an EphB4 activity. The isolated antibody or antigen binding portion thereof may binds to an epitope situated within amino acids 16-198 of the EphB4 sequence of FIG. 1. For example, the epitope may be situated within the Globular Domain (GD) of EphB4 that binds to EphrinB2. The isolated antibody or antigen binding portion thereof may inhibit the binding of EphB4 to the extracellular portion of EphrinB2. The isolated antibody or antigen binding portion thereof may bind to an epitope situated within amino acids 324-429 or 430-537 of the EphB4 sequence of FIG. 1. For example, the isolated antibody or antigen binding portion thereof may bind to the first fibronectin-like domain (FND1) or the second fibronectin-like domain (FND2) of EphB4. The isolated antibody or antigen binding portion thereof may inhibit EphB4 dimerization or multimerization and may optionally inhibit the EphrinB2-stimulated autophosphorylation of EphB4. The isolated antibody or antigen binding portion thereof may inhibit the formation of tubes by cultured endothelial cells, the vascularization of a tissue in vivo, the vascularization of tissue implanted in the cornea of an animal, the vascularization of a Matrigel tissue plug implanted in an animal, and/or the growth of a human tumor xenograft in a mouse. Preferred antibodies that bind to an epitope situated within amino acids 16-198 of the EphB4 sequence of FIG. 1 include antibodies denoted herein as No. 001, No. 023, No. 035, and No. 079. Preferred antibodies that bind to an epitope situated within amino acids 428-537 of the EphB4 sequence of FIG. 1 include antibodies denoted herein as No. 047, No. 057, No. 851-1, No. 098, and No. 138.

In certain aspects, the disclosure provides an isolated antibody or antigen binding portion thereof that binds to an epitope situated in the extracellular portion of EphB4 and stimulates EphB4 kinase activity. For example, described herein are isolated antibodies or antigen binding portion thereof that bind to an epitope situated within amino acids 324-429 or 430-537 of the EphB4 sequence of FIG. 1 and stimulate EphB4 kinase activity. The isolated antibody or antigen binding portion thereof may bind to FND1 or FND2 of EphB4. The antibody may be selected from the group consisting of antibodies denoted herein as No. 85L, No. 091, No. 121, and No. 131.

The disclosure provides humanized versions of any of the antibodies disclosed herein, as well as antibodies and antigen binding portions thereof that comprise at least one CDR portion derived from an antibody disclosed herein, particularly the CDR3. In preferred embodiments, the antibody is a monoclonal antibody that is immunocompatible with the subject to which it is to be administered, and preferably is clinically acceptable for administration to a human.

In certain aspects, the disclosure provides a hybridoma that produces an antibody disclosed herein, and particularly a hybridoma that produces an antibody selected from the group consisting of antibodies denoted herein as No. 001, No. 023, No. 035, No. 079, No. 047, No. 057, No. 85H, No. 098, No. 138, No. 085L, NO. 091, and No. 131. Hybridomas producing antibody No. 023 (epitope within amino acids 16-198), antibody No. 091 (kinase activating antibody; epitope within amino acids 324-429), antibody No. 098 (epitope within amino acids 430-537), antibody No. 131 (epitope within amino acids 324-429), and antibody No. 138 epitope within amino acids 430-537) were deposited in the American Type Culture Collection (ATCC), 10801 University Boulevard, Manassas, Va. 20110-2209. The ATCC Deposit Designation Nos. for antibody No. 023, No. 47, No. 091, No. 098, No. 131, and No. 138 are PTA-6208, PTA-11338, PTA-6209, PTA-6210, PTA-6214 and PTA-6211, respectively.

Therefore, certain aspects of the disclosure provide a hybridoma cell having an ATCC Deposit Designation No. selected from the group consisting of PTA-6208, PTA-11338, PTO-6209, PTA-6210, PTA-6214, AND PTA-6211.

Surprisingly, antibodies that inhibit ligand binding, antibodies that inhibit EphB4 kinase activation and antibodies that activate EphB4 kinase activity all inhibit EphB4 mediated events in bioassays. Accordingly, the disclosure provides a method of treating cancer, the method comprising administering to a patient in need thereof an effective amount of an isolated antibody or antigen binding portion thereof that binds to an epitope situated in the extracellular portion of EphB4 and either inhibits an EphB4 activity or activates EphB4 kinase activity. Optionally the patient has been diagnosed with a cancer selected from the group consisting of colon carcinoma, breast tumor, mesothelioma, prostate tumor, squamous cell carcinoma, Kaposi sarcoma, and leukemia. The isolated antibody or antigen binding portion thereof may be administered systemically or locally. Additionally, the disclosure provides methods of inhibiting angiogenesis in a patient, the method comprising administering to a patient in need thereof an effective amount of an isolated antibody or antigen binding portion thereof that binds to an epitope situated in the extracellular portion of EphB4 and inhibits an EphB4 activity or activates an EphB4 kinase activity. Optionally, the patient is diagnosed macular degeneration.

In certain aspects, the disclosure provides a pharmaceutical preparation comprising any of the isolated antibodies or antigen binding portions thereof disclosed herein, as well as the use of such antibodies or antigen binding portions thereof to make a pharmaceutical preparation for treating cancer. Optionally, the cancer is selected from the group consisting of colon carcinoma, breast tumor, mesothelioma, prostate tumor, squamous cell carcinoma, Kaposi sarcoma, and leukemia.

In certain aspects, the antibodies disclosed herein may be covalently linked (or otherwise stably associated with) an additional functional moiety, such as a label or a moiety that confers desirable pharmacokinetic properties. Exemplary labels include those that are suitable for detection by a method selected from the group consisting of fluorescence detection methods, positron emission tomography detection methods and nuclear magnetic resonance detection methods. Labels may, for example, be selected from the group consisting of a fluorescent label, a radioactive label, and a label having a distinctive nuclear magnetic resonance signature. Moieties such as a polyethylene glycol (PEG) moiety may be affixed to an antibody or antigen binding portion thereof to increase serum half-life.

BRIEF DESCRIPTION OF THE DRAWINGS

FIG. 1 shows an amino acid sequence of human EphB4 precursor protein (SEQ ID NO: 1).

FIG. 2 shows a cDNA nucleotide sequence of human EphB4 protein (SEQ ID NO: 2).

FIG. 3 shows amino acid sequence of the B4ECv3 protein (predicted sequence of the precursor including uncleaved Eph B4 leader peptide is shown) (SEQ ID NO: 3).

FIG. 4 shows amino acid sequence of the B4ECv3NT protein (predicted sequence of the precursor including uncleaved Eph B4 leader peptide is shown) (SEQ ID NO: 4).

FIG. 5 shows the monoclonal antibodies generated against EphB4 and epitope mapping of these antibodies. The topology of the EphB4 extracellular domain is shown, including a globular domain (G), a cystein-rich domain (C), and two fibronectin type 3 domains (F1 and F2).

FIG. 9 shows that EphB4 antibodies inhibit the growth of SCC15 xenograft tumors.

FIG. 10 shows that EphB4 antibodies cause apoptosis, necrosis and decreased angiogenesis in SCC15, head and neck carcinoma tumor type.

FIG. 11 shows that systemic administration of EphB4 antibodies leads to tumor regression.

DETAILED DESCRIPTION OF THE INVENTION

Figure 6A:
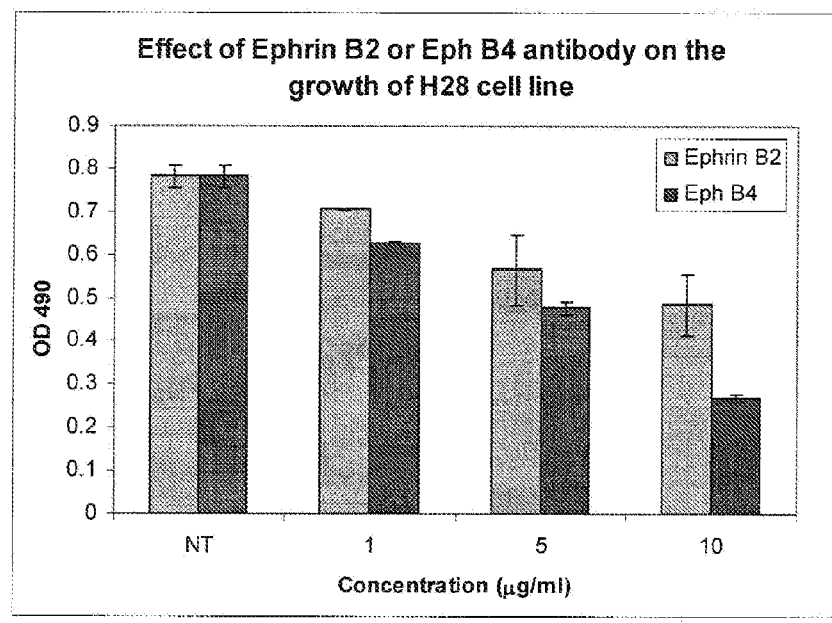
FIG. 6 shows effects of Ephrin 132 polyclonal antibodies and EphB4 polyclonal antibodies tumor cell growth. A) H28 cell line; B) H2373 cell line; and C) H2052 cell line.

I. EphB4 Antibodies and Other Binding Polypeptides

The disclosure provides, in part, defined portions of the EphB4 molecule that can be effectively targeted by polypeptide binding agents, such as antibodies, antigen binding portions of antibodies, and non-immunoglobulin antigen binding scaffolds. The EphB4 polypeptide binding agents described herein may be used to treat a variety of disorders, particularly cancers and disorders related to unwanted angiogenesis. The disclosure provides antibodies and antigen binding portions thereof that inhibit one or more EphB4 mediated functions, such as EphrinB2 binding or EphB4 kinase activity. Such binding agents may be used to inhibit EphB4 function in vitro and in vivo, and preferably for treating cancer or disorders associated with unwanted angiogenesis. The disclosure also provides antibodies and antigen binding portions thereof that activate EphB4 kinase activity (typically assessed by evaluating EphB4 phosphorylation state). Surprisingly, such antibodies also inhibit EphB4 functions in cell based and in vivo assays. Accordingly, such binding agents may be used to inhibit EphB4 function in vitro and in vivo, and preferably for treating cancer or disorders associated with unwanted angiogenesis. While not wishing to be limited to any particular mechanism, it is expected that these antibodies stimulate not only EphB4 kinase activity, but also EphB4 removal from the membrane, thus decreasing overall EphB4 levels.

EphB4 belongs to a family of transmembrane receptor protein tyrosine kinases. The extracellular portion of EphB4 is composed of the ligand-binding domain (also referred to as globular domain), a cysteine-rich domain, and a pair of fibronectin type III repeats (e.g., see FIG. 1). The cytoplasmic domain consists of a juxtamembrane region containing two conserved tyrosine residues; a protein tyrosine kinase domain; a sterile α-motif (SAM) and a PDZ-domain binding motif. EphB4 is specific for the membrane-bound ligand Ephrin B2 (Sakano, S. et al 1996; Brambilla R. et al 1995). EphB4 is activated by binding of clustered, membrane-attached ephrin ligands (Davis S et al, 1994), indicating that contact between cells expressing the receptor and cells expressing the ligand is required for the Eph receptor activation. Upon ligand binding, an EphB4 receptor dimerizes and autophosphorylates the juxtamembrane tyrosine residues to acquire full activation.

As used herein, the term "EphB4" refers to an EphB4 polypeptide from a mammal including humans. In one embodiment, the antibodies (immunoglobulins) are raised against an isolated and/or recombinant mammalian EphB4 or portion thereof (e.g., peptide) or against a host cell which expresses recombinant mammalian EphB4. In certain aspects, antibodies of the invention specifically bind to an extracellular domain of an EphB4 protein (referred to herein as an EphB4 soluble polypeptide). For example, an EphB4 soluble polypeptide comprises a globular domain and is capable of binding to Ephrin B2. An example of EphB4 soluble polypeptides is provided in FIG. 2. As used herein, the EphB4 soluble polypeptides include fragments, functional variants, and modified forms of EphB4 soluble polypeptide.

An "immunoglobulin" is a tetrameric molecule. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites. Immunoglobulins may be organized into higher order structures. IgA is generally a dimer of two tetramers. IgM is generally a pentamer of five tetramers.

Immunoglobulin chains exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminus to C-terminus, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987); Chothia et al. Nature 342:878-883 (1989).

An "antibody" refers to an intact immunoglobulin or to an antigen-binding portion thereof that competes with the intact antibody for specific binding. Antigen-binding portions may be produced by recombinant DNA techniques or by enzymatic or chemical cleavage of intact antibodies. Antigen-binding portions include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms "anti-EphB4 antibody" and "EphB4 antibody" are used interchangeably herein.

An Fab fragment is a monovalent fragment consisting of the VL, VH, CL and CH I domains; a F(ab').sub.2 fragment is a bivalent fragment comprising two Fab fragments linked by a disulfide bridge at the hinge region; a Fd fragment consists of the VH and CH1 domains; an Fv fragment consists of the VL and VH domains of a single arm of an antibody; and a dAb fragment (Ward et al., Nature 341:544-546, 1989) consists of a VH domain.

A single-chain antibody (scFv) is an antibody in which a VL and VH regions are paired to form a monovalent molecules via a synthetic linker that enables them to be made as a single protein chain (Bird et al., Science 242:423-426, 1988 and Huston et al., Proc. Natl. Acad. Sci. USA 85:5879-5883, 1988). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., Proc. Natl. Acad. Sci. USA 90:6444-6448, 1993, and Poljak, R. J., et al., Structure 2:1121-1123, 1994). One or more CDRs may be incorporated into a molecule either covalently or noncovalently.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a "bispecific" or "bifunctional" antibody has two different binding sites.

The term "human antibody" includes all antibodies that have one or more variable and constant regions derived from human immunoglobulin sequences. In a preferred embodiment, all of the variable and constant domains are derived from human immunoglobulin sequences (a fully human antibody). These antibodies may be prepared in a variety of ways, as described below.

The term "chimeric antibody" refers to an antibody that contains one or more regions from one antibody and one or more regions from one or more other antibodies. In a preferred embodiment, one or more of the CDRs are derived from a human anti-EphB4 antibody. In a more preferred embodiment, all of the CDRs are derived from a human anti-EphB4 antibody. In another preferred embodiment, the CDRs from more than one human anti-EphB4 antibodies are mixed and matched in a chimeric antibody. For instance, a chimeric antibody may comprise a CDR1 from the light chain of a first human anti-EphB4 antibody may be combined with CDR2 and CDR3 from the light chain of a second human anti-EphB4 antibody, and the CDRs from the heavy chain may be derived from a third anti-EphB4 antibody. Further, the framework regions may be derived from one of the same anti-EphB4 antibodies, from one or more different antibodies, such as a human antibody, or from a humanized antibody.

A "neutralizing antibody" is an antibody that inhibits the binding of EphB4 to EphrinB2 when an excess of the anti-EphB4 antibody reduces the amount of EphB4 (soluble) bound to EphrinB2 by at least about 20% and preferably by at least 40%, more preferably 60%, even more preferably 80%, or even more preferably 85%. The binding reduction may be measured by any means known to one of ordinary skill in the art, for example, as measured in an in vitro competitive binding assay. An example of measuring the reduction in binding is presented below in the Examples.

An "EphB4 kinase activating antibody" is an antibody that activates EphB4 kinase activity by at least about 20% when added to a cell, tissue or organism expressing EphB4. In a preferred embodiment, the antibody activates EphB4 kinase activity by at least 40%, more preferably 60%, even more preferably 80%, or even more preferably 85%. Typically kinase activity is measured as the phosphorylation state of EphB4 itself (tyrosine autophosphorylation).

As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following radioisotopes or radionuclides (e.g., 3H, 14C, 15N, 35S, 90Y, 99Tc; 111In, 125I, 131I), fluorescent labels (e.g., FITC, rhodamine, lanthanide phosphors), enzymatic labels (e.g., horseradish peroxidase, beta-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

As shown in the Examples below, Applicants have generated a number of monoclonal antibodies against EphB4 as well as hybridoma cell lines producing EphB4 monoclonal antibodies. These antibodies were further characterized in many ways, such as, their ability to inhibit interaction between EphB4 and its ligand (e.g., Ephrin B2—neutralizing antibodies), their ability to inhibit dimerization or multimerization of EphB4 receptor, their ability to induce tyrosine phosphorylation of EphB4, their cross-reactivity with other Eph family members, their ability to inhibit angiogenesis, and their ability to inhibit tumor growth. Further, epitope mapping studies reveals that these EphB4 antibodies may specifically bind to one or more regions of EphB4 (e.g., a globular domain, a cystein-rich domain, or a fibronectin type III domain). For example, an EphB4 antibody may bind to both fibronectin type III domains.

In certain aspects, antibodies of the invention specifically bind to an extracellular domain (ECD) of an EphB4 protein (also referred to herein as a soluble EphB4 polypeptide). A soluble EphB4 polypeptide may comprise a sequence encompassing the globular (G) domain (amino acids 29-197 of SEQ ID NO: 1), and optionally additional domains, such as the cysteine-rich domain (amino acids 239-321 of SEQ ID NO: 1), the first fibronectin type 3 domain (amino acids 324-429 of SEQ ID NO: 1) and the second fibronectin type 3 domain (amino acids 434-526 of SEQ ID NO: 1). Exemplary EphB4 soluble polypeptides are provided in FIGS. 3-4. As used herein, the EphB4 soluble polypeptides include fragments, functional variants, and modified forms of EphB4 soluble polypeptide.

In certain aspects, the present invention provides antibodies (anti-EphB4) having binding specificity for an EphB4 or a portion of EphB4. Examples of these antibodies include, but are not limited to, EphB4 antibody Nos. 1, 23, 35, 47, 57, 79, 85L, 85H, 91, 98, 121, 131, and 138 as shown in FIG. 5. Optionally, the immunoglobulins can bind to EphB4 with an affinity of at least about $1 \times 10^{-6}$, $1 \times 10^{-7}$, $1 \times 10^{-8}$, $1 \times 10^{-9}$ M or less. Optionally, antibodies and portions thereof bind to EphrinB2 with an affinity that is roughly equivalent to that of a soluble extracellular EphB4 polypeptide comprising the globular ligand binding domain.

Antibodies disclosed herein will preferably be specific for EphB4, with minimal binding to other members of the Eph or Ephrin families. In another aspect of the invention, the anti-EphB4 antibody demonstrates both species and molecule selectivity. In one embodiment, the anti-EphB4 antibody binds to human, cynomologous or rhesus EphB4. In a preferred embodiment, the anti-EphB4 antibody does not bind to mouse, rat, guinea pig, dog or rabbit EphB4. Optionally, the antibody does bind to multiple different EphB4s from different species, such as human and mouse. Following the teachings of the specification, one may determine the species selectivity for the anti-EphB4 antibody using methods well known in the art. For instance, one may determine species selectivity using Western blot, FACS, ELISA or RIA. In a preferred embodiment, one may determine the species selectivity using Western blot. In another embodiment, the anti-EphB4 antibody has a tendency to bind EphB4 that is at least 50 times greater than its tendency to bind other members of the EphB family from the same species, and preferably 100 or 200 times greater. One may determine selectivity using methods well known in the art following the teachings of the specification. For instance, one may determine the selectivity using Western blot, FACS, ELISA or RIA. In a preferred embodiment, one may determine the molecular selectivity using Western blot.

In certain embodiments, antibodies of the present invention bind to one or more specific domains of EphB4. For example, an antibody binds to one or more extracellular domains of EphB4 (such as the globular domain, the cystein-rich domain, and the first fibronectin type 3 domain, and the second fibronectin type 3 domain). For example, EphB4 antibody Nos. 1, 23, 35, and 79 bind to an epitope in the region spanning amino acids 16-198 of the sequence in FIG. 1, spanning the globular domain. EphB4 antibody Nos. 85L, 85H, 91, and 131 bind to an epitope in the region spanning amino acids 324-429, including the first fibronectin type 3 domain. EphB4 antibody Nos. 47, 57, 85H, 98, 121, and 138 bind to an epitope in the region spanning amino acids 430-537, including the second fibronectin type 3 domain. Optionally, the subject antibody (e.g., EphB4 antibody No. 85H) can bind to at least two domains of an EphB4 (FIG. 5).

The anti-EphB4 antibody may be an IgG, an IgM, an IgE, an IgA or an IgD molecule. In a preferred embodiment, the antibody is an IgG and is an IgG1, IgG2, IgG3 or IgG4 subtype. In a more preferred embodiment, the anti-EphB4 antibody is subclass IgG2. The class and subclass of EphB4 antibodies may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies. To illustrate, the classes and subclasses of the exemplary EphB4 antibodies are shown in Table 1 below.

In certain embodiments, single chain antibodies, and chimeric, humanized or primatized (CDR-grafted) antibodies, as well as chimeric or CDR-grafted single chain antibodies, comprising portions derived from different species, are also encompassed by the present invention as antigen binding portions of an antibody. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125, 023; Boss et al., U.S. Pat. No. 4,816,397; Boss et al., European Patent No. 0,120,694; Neuberger, M. S. et al., WO 86/01533; Neuberger, M. S. et al., European Patent No. 0,194, 276 B1; Winter, U.S. Pat. No. 5,225,539; and Winter, European Patent No. 0,239,400 B1. See also, Newman, R. et al., BioTechnology, 10: 1455-1460 (1992), regarding primatized antibody. See, e.g., Ladner et al., U.S. Pat. No. 4,946,778; and Bird, R. E. et al., Science, 242: 423-426 (1988)), regarding single chain antibodies.

In addition, functional fragments of antibodies, including fragments of chimeric, humanized, primatized or single chain antibodies, can also be produced. Functional fragments of the subject antibodies retain at least one binding function and/or modulation function of the full-length antibody from which they are derived. Preferred functional fragments retain an antigen binding function of a corresponding full-length antibody (e.g., specificity for an EphB4). Certain preferred functional fragments retain the ability to inhibit one or more functions characteristic of an EphB4, such as a binding activity, a signaling activity, and/or stimulation of a cellular response. For example, in one embodiment, a functional fragment of an EphB4 antibody can inhibit the interaction of EphB4 with one or more of its ligands (e.g., Ephrin B2) and/or can inhibit one or more receptor-mediated functions, such as cell migration, cell proliferation, angiogenesis, and/or tumor growth.

For example, antibody fragments capable of binding to an EphB4 receptor or portion thereof, including, but not limited to, Fv, Fab, Fab' and F(ab')$_2$ fragments are encompassed by the invention. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the $CH_1$ domain and hinge region of the heavy chain.

A humanized antibody is an antibody that is derived from a non-human species, in which certain amino acids in the framework and constant domains of the heavy and light chains have been mutated so as to avoid or abrogate an immune response in humans. Alternatively, a humanized antibody may be produced by fusing the constant domains from a human antibody to the variable domains of a non-human species. Examples of how to make humanized antibodies may be found in U.S. Pat. Nos. 6,054,297, 5,886,152 and 5,877, 293. A humanized antibody may comprise portions of immunoglobulins of different origin, wherein optionally at least one portion is of human origin. Accordingly, the present invention relates to a humanized immunoglobulin having binding specificity for an EphB4 (e.g., human EphB4), said immunoglobulin comprising an antigen binding region of nonhuman origin (e.g., rodent) and at least a portion of an immunoglobulin of human origin (e.g., a human framework region, a human constant region or portion thereof). For example, the humanized antibody can comprise portions derived from an immunoglobulin of nonhuman origin with the requisite specificity, such as a mouse, and from immunoglobulin sequences of human origin (e.g., a chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain).

Another example of a humanized immunoglobulin of the present invention is an immunoglobulin containing one or more immunoglobulin chains comprising a CDR of nonhuman origin (e.g., one or more CDRs derived from an antibody of nonhuman origin) and a framework region derived from a light and/or heavy chain of human origin (e.g., CDR-grafted antibodies with or without framework changes). In one embodiment, the humanized immunoglobulin can compete with murine monoclonal antibody for binding to an EphB4 polypeptide. Chimeric or CDR-grafted single chain antibodies are also encompassed by the term humanized immunoglobulin.

In certain embodiments, the present invention provides EphB4 antagonist antibodies. As described herein, the term "antagonist antibody" refers to an antibody that can inhibit one or more functions of an EphB4, such as a binding activity (e.g., ligand binding) and a signaling activity (e.g., clustering or phosphorylation of EphB4, stimulation of a cellular response, such as stimulation of cell migration or cell proliferation). For example, an antagonist antibody can inhibit (reduce or prevent) the interaction of an EphB4 receptor with a natural ligand (e.g., Ephrin B2 or fragments thereof). Preferably, antagonist antibodies directed against EphB4 can inhibit functions mediated by EphB4, including endothelial cell migration, cell proliferation, angiogenesis, and/or tumor growth. Optionally, the antagonist antibody binds to an extracellular domain of EphB4.

In other embodiments, the present invention provides EphB4 kinase activating antibodies. Such antibodies enhance EphB4 kinase activity, even independent of EphrinB2. In some instances, such antibodies may be used to stimulate EphB4. However, applicants note that in most cell-based and in vivo assays, such antibodies surprisingly behaved like antagonist antibodies. Such antibodies appear to bind to at least one of the two fibronectin type III domains, particularly the region of amino acids 324-429 of FIG. 1.

In certain embodiments, anti-idiotypic antibodies are also provided. Anti-idiotypic antibodies recognize antigenic determinants associated with the antigen-binding site of another antibody. Anti-idiotypic antibodies can be prepared against a second antibody by immunizing an animal of the same species, and preferably of the same strain, as the animal used to produce the second antibody. See e.g., U.S. Pat. No. 4,699,880. In one embodiment, antibodies are raised against receptor or a portion thereof, and these antibodies are used in turn to produce an anti-idiotypic antibody. The anti-idiotypic antibodies produced thereby can bind compounds which bind receptor, such as ligands of receptor function, and can be used in an immunoassay to detect or identify or quantitate such compounds. Such an anti-idotypic antibody can also be an inhibitor of an EphB4 receptor function, although it does not bind receptor itself. Such an anti-idotypic antibody can also be called an antagonist antibody.

In certain aspects, the present invention provides the hybridoma cell lines, as well as to the monoclonal antibodies produced by these hybridoma cell lines. The cell lines of the present invention have uses other than for the production of the monoclonal antibodies. For example, the cell lines of the present invention can be fused with other cells (such as suitably drug-marked human myeloma, mouse myeloma, human-mouse heteromyeloma or human lymphoblastoid cells) to produce additional hybridomas, and thus provide for the transfer of the genes encoding the monoclonal antibodies. In addition, the cell lines can be used as a source of nucleic acids encoding the anti-EphB4 immunoglobulin chains, which can be isolated and expressed (e.g., upon transfer to other cells using any suitable technique (see e.g., Cabilly et al., U.S. Pat. No. 4,816,567; Winter, U.S. Pat. No. 5,225,539)). For instance, clones comprising a rearranged anti-EphB4 light or heavy chain can be isolated (e.g., by PCR) or cDNA libraries can be prepared from mRNA isolated from the cell lines, and cDNA clones encoding an anti-EphB4 immunoglobulin chain can be isolated. Thus, nucleic acids encoding the heavy and/or light chains of the antibodies or portions thereof can be obtained and used in accordance with recombinant DNA techniques for the production of the specific immunoglobulin, immunoglobulin chain, or variants thereof (e.g., humanized immunoglobulins) in a variety of host cells or in an in vitro translation system. For example, the nucleic acids, including cDNAs, or derivatives thereof encoding variants such as a humanized immunoglobulin or immunoglobulin chain, can be placed into suitable prokaryotic or eukaryotic vectors (e.g., expression vectors) and introduced into a suitable host cell by an appropriate method (e.g., transformation, transfection, electroporation, infection), such that the nucleic acid is operably linked to one or more expression control elements (e.g., in the vector or integrated into the host cell genome). For production, host cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded protein can be recovered and/or isolated (e.g., from the host cells or medium). It will be appreciated that the method of production encompasses expression in a host cell of a transgenic animal (see e.g., WO 92/03918, GenPharm International, published Mar. 19, 1992).

II. Methods of Antibody Production

Preparation of immunizing antigen, and polyclonal and monoclonal antibody production can be performed as described herein, or using other suitable techniques. A variety of methods have been described. See e.g., Kohler et al., Nature, 256: 495-497 (1975) and Eur. J. Immunol. 6: 511-519 (1976); Milstein et al., Nature 266: 550-552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer 94), Ausubel, F. M. et al., Eds., (John Wiley & Sons: New York, N.Y.), Chapter 11, (1991). Generally, a hybridoma can be produced by fusing a suitable immortal cell line (e.g., a myeloma cell line such as SP2/0) with antibody producing cells. The antibody producing cell, preferably those of the spleen or lymph nodes, are obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies. See e.g., Jakobovits et al., Proc. Natl. Acad. Sci. USA, 90: 2551-2555 (1993); Jakobovits et al., Nature, 362: 255-258 (1993); Lonberg et al., U.S. Pat. No. 5,545,806; Surani et al., U.S. Pat. No. 5,545,807.

To illustrate, immunogens derived from an EphB4 polypeptide (e.g., an EphB4 polypeptide or an antigenic fragment thereof which is capable of eliciting an antibody response, or an EphB4 fusion protein) can be used to immunize a mammal, such as a mouse, a hamster or rabbit. See, for example, Antibodies: A Laboratory Manual ed. by Harlow and Lane (Cold Spring Harbor Press: 1988). Techniques for conferring immunogenicity on a protein or peptide include conjugation to carriers or other techniques well known in the art. An immunogenic portion of an EphB4 polypeptide can be administered in the presence of adjuvant. The progress of immunization can be monitored by detection of antibody titers in plasma or serum. Standard ELISA or other immunoassays can be used with the immunogen as antigen to assess the levels of antibodies. In one embodiment, antibodies of the invention are specific for the extracellular portion of the EphB4 protein (e.g., SEQ ID NO: 2) or fragments thereof. In another embodiment, antibodies of the invention are specific for the intracellular portion or the transmembrane portion of the EphB4 protein.

Following immunization of an animal with, an antigenic preparation of an EphB4 polypeptide, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with an EphB4 polypeptide and monoclonal antibodies isolated from a culture comprising such hybridoma cells.

In certain embodiments, antibodies of the present invention can be fragmented using conventional techniques and the fragments screened for utility in the same manner as described above for whole antibodies. For example, F(ab)2 fragments can be generated by treating antibody with pepsin. The resulting F(ab)2 fragment can be treated to reduce disulfide bridges to produce Fab fragments.

In certain embodiments, antibodies of the present invention are further intended to include bispecific, single-chain, and chimeric and humanized molecules having affinity for an EphB4 polypeptide conferred by at least one CDR region of the antibody. Techniques for the production of single chain antibodies (U.S. Pat. No. 4,946,778) can also be adapted to produce single chain antibodies. Also, transgenic mice or other organisms including other mammals, may be used to express humanized antibodies. Methods of generating these antibodies are known in the art. See, e.g., Cabilly et al., U.S. Pat. No. 4,816,567; Cabilly et al., European Patent No. 0,125,023; Queen et al., European Patent No. 0,451,216; Boss et al., U.S. Pat. No. 4,816,397; Boss et al., European Patent No. 0,120,694; Neuberger, M. S. et al., WO 86/01533; Neuberger, M. S. et al., European Patent No. 0,194,276; Winter, U.S. Pat. No. 5,225,539; winter, European Patent No. 0,239,400; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., Science, 242: 423-426 (1988)).

Such humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

In certain embodiments, the antibodies are further attached to a label that is able to be detected (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography. Immunoscintigraphy using antibodies or other binding polypeptides directed at EphB4 may be used to detect and/or diagnose cancers and vasculature. For example, monoclonal antibodies against the EphB4 marker labeled with $^{99}$Technetium, $^{111}$Indium, $^{125}$Iodine-may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, preferably 1-10 millicuries, most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

In certain preferred embodiments, an antibody of the invention is a monoclonal antibody, and in certain embodiments the invention makes available methods for generating novel antibodies. For example, a method for generating a monoclonal antibody that binds specifically to an EphB4 polypeptide may comprise administering to a mouse an amount of an immunogenic composition comprising the EphB4 polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the EphB4 polypeptide. Once obtained, a hybridoma can be propagated in a cell culture, optionally in culture conditions where the hybridoma-derived cells produce the monoclonal antibody that binds specifically to EphB4 polypeptide. The monoclonal antibody may be purified from the cell culture.

In addition, the techniques used to screen antibodies in order to identify a desirable antibody may influence the properties of the antibody obtained. For example, an antibody to be used for certain therapeutic purposes will preferably be able to target a particular cell type. Accordingly, to obtain antibodies of this type, it may be desirable to screen for antibodies that bind to cells that express the antigen of interest (e.g., by fluorescence activated cell sorting). Likewise, if an antibody is to be used for binding an antigen in solution, it may be desirable to test solution binding. A variety of different techniques are available for testing antibody:antigen interactions to identify particularly desirable antibodies. Such techniques include ELISAs, surface plasmon resonance binding assays (e.g., the Biacore binding assay, Bia-core AB, Uppsala, Sweden), sandwich assays (e.g., the paramagnetic bead system of IGEN International, Inc., Gaithersburg, Md.), western blots, immunoprecipitation assays and immunohistochemistry.

The antibodies of the present invention are useful in a variety of applications, including research, diagnostic and therapeutic applications. For instance, they can be used to isolate and/or purify receptor or portions thereof, and to study receptor structure (e.g., conformation) and function.

III. Diagnostic Applications

In certain aspects, the various antibodies of the present invention can be used to detect or measure the expression of EphB4 receptor, for example, on endothelial cells (e.g., venous endothelial cells), or on cells transfected with an EphB4 receptor gene. Thus, they also have utility in applications such as cell sorting and imaging (e.g., flow cytometry, and fluorescence activated cell sorting), for diagnostic or research purposes.

In certain embodiments, the antibodies or antigen binding fragments of the antibodies can be labeled or unlabeled for diagnostic purposes. Typically, diagnostic assays entail detecting the formation of a complex resulting from the binding of an antibody to EphB4. The antibodies can be directly labeled. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the antibodies can be used in assays, such as agglutination assays. Unlabeled antibodies can also be used in combination with another (one or more) suitable reagent which can be used to detect antibody, such as a labeled antibody (e.g., a second antibody) reactive with the first antibody (e.g., anti-idiotype antibodies or other antibodies that are specific for the unlabeled immunoglobulin) or other suitable reagent (e.g., labeled protein A). An EphB4 antibody may also be derivatized with a chemical group such as polyethylene glycol (PEG), a methyl or ethyl group, or a carbohydrate group. These groups may be useful to improve the biological characteristics of the antibody, e.g., to increase serum half-life or to increase tissue binding.

In one embodiment, the antibodies of the present invention can be utilized in enzyme immunoassays, wherein the subject antibodies, or second antibodies, are conjugated to an enzyme. When a biological sample comprising an EphB4 protein is combined with the subject antibodies, binding occurs between the antibodies and EphB4 protein. In one embodiment, a sample containing cells expressing an EphB4 protein (e.g., endothelial cells) is combined with the subject antibodies, and binding occurs between the antibodies and cells bearing an EphB4 protein comprising an epitope recognized by the antibody. These bound cells can be separated from unbound reagents and the presence of the antibody-enzyme conjugate specifically bound to the cells can be determined, for example, by contacting the sample with a substrate of the enzyme which produces a color or other detectable change when acted on by the enzyme. In another embodiment, the subject antibodies can be unlabeled, and a second, labeled antibody can be added which recognizes the subject antibody.

In certain aspects, kits for use in detecting the presence of an EphB4 protein in a biological sample can also be prepared. Such kits will include an antibody which binds to an EphB4 protein or portion of said receptor, as well as one or more ancillary reagents suitable for detecting the presence of a complex between the antibody and EphB4 or portion thereof. The antibody compositions of the present invention can be provided in lyophilized form, either alone or in combination with additional antibodies specific for other epitopes. The antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies can be provided as a lyophilized mixture with the adjunct ingredients, or the adjunct ingredients can be separately provided for combination by the user. Generally these adjunct materials will be present in less than about 5% weight based on the amount of active antibody, and usually will be present in a total amount of at least about 0.001% weight based on antibody concentration. Where a second antibody capable of binding to the monoclonal antibody is employed, such antibody can be provided in the kit, for instance in a separate vial or container. The second antibody, if present, is typically labeled, and can be formulated in an analogous manner with the antibody formulations described above.

Similarly, the present invention also relates to a method of detecting and/or quantitating expression of an EphB4 or portion of the receptor by a cell, wherein a composition comprising a cell or fraction thereof (e.g., membrane fraction) is contacted with an antibody which binds to an EphB4 or portion of the receptor under conditions appropriate for binding of the antibody thereto, and antibody binding is monitored. Detection of the antibody, indicative of the formation of a complex between antibody and EphB4 or a portion thereof, indicates the presence of the receptor. Binding of antibody to the cell can be determined by standard methods, such as those described in the working examples. The method can be used to detect expression of EphB4 on cells from an individual. Optionally, a quantitative expression of EphB4 on the surface of endothelial cells can be evaluated, for instance, by flow cytometry, and the staining intensity can be correlated with disease susceptibility, progression or risk.

The present invention also relates to a method of detecting the susceptibility of a mammal to certain diseases. To illustrate, the method can be used to detect the susceptibility of a mammal to diseases which progress based on the amount of EphB4 present on cells and/or the number of EphB4-positive cells in a mammal. In one embodiment, the invention relates to a method of detecting susceptibility of a mammal to a tumor. In this embodiment, a sample to be tested is contacted with an antibody which binds to an EphB4 or portion thereof under conditions appropriate for binding of said antibody thereto, wherein the sample comprises cells which express EphB4 in normal individuals. The binding of antibody and/or amount of binding is detected, which indicates the susceptibility of the individual to a tumor, wherein higher levels of receptor correlate with increased susceptibility of the individual to a tumor. Applicants and other groups have found that expression of EphB4 has a correlation with tumor growth and progression. The antibodies of the present invention can also be used to further elucidate the correlation of EphB4 expression with progression of angiogenesis-associated diseases in an individual.

IV. Therapeutic Applications

In certain embodiments, the present invention provides compositions and methods for inhibiting angiogenesis and for treating angiogenesis-associated diseases (or disorders). In other embodiments, the present invention provides methods of inhibiting or reducing tumor growth and methods of treating an individual suffering from cancer. These methods involve administering to the individual a therapeutically effective amount of one or more EphB4 antibodies as described above. These methods are particularly aimed at therapeutic and prophylactic treatments of animals, and more particularly, humans.

As described herein, angiogenesis-associated diseases include, but are not limited to, angiogenesis-dependent cancer, including, for example, solid tumors, blood born tumors such as leukemias, and tumor metastases; benign tumors, for example, hemangiomas, acoustic neuromas, neurofibromas, trachomas, and pyogenic granulomas; inflammatory disorders such as immune and non-immune inflammation; chronic articular rheumatism and psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation and wound healing;

telangiectasia psoriasis scleroderma, pyogenic granuloma, cororany collaterals, ischemic limb angiogenesis, corneal diseases, rubeosis, arthritis, diabetic neovascularization, fractures, vasculogenesis, hematopoiesis.

It is understood that methods and compositions of the invention are also useful for treating angiogenesis-independent cancers (tumors). As used herein, the term "angiogenesis-independent cancer" refers to a cancer (tumor) where there is no or little neovascularization in the tumor tissue.

In particular, antibodies of the present invention are useful for treating or preventing a cancer (tumor), including, but not limited to, colon carcinoma, breast cancer, mesothelioma, prostate cancer, bladder cancer, squamous cell carcinoma of the head and neck (HNSCC), Kaposi sarcoma, and leukemia.

In certain embodiments of such methods, one or more EphB4 antibodies can be administered, together (simultaneously) or at different times (sequentially). In addition, antibodies can be administered with another agent for treating cancer or for inhibiting angiogenesis. In a specific embodiment, the subject antibodies of the present invention can also be used with other antibody therapeutics (monoclonal or polyclonal).

In certain embodiments, the subject antibodies of the invention can be used alone. Alternatively, the subject antibodies may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present invention recognizes that the effectiveness of conventional cancer therapies (e.g., chemotherapy, radiation therapy, phototherapy, immunotherapy, and surgery) can be enhanced through the use of one or more EphB4 antibodies of the invention.

A wide array of conventional compounds have been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a subject EphB4 antibody of the present invention is administered in combination with another conventional antineoplastic agent, either concomitantly or sequentially, such antibody is shown to enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In certain embodiments, pharmaceutical compounds that may be used for combinatory anti-angiogenesis therapy include: (1) inhibitors of release of "angiogenic molecules," such as bFGF (basic fibroblast growth factor); (2) neutralizers of angiogenic molecules, such as an anti-βbFGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like. For additional proposed inhibitors of angiogenesis, see Blood et al., Bioch. Biophys. Acta., 1032:89-118 (1990), Moses et al., Science, 248:1408-1410 (1990), Ingber et al., Lab. Invest., 59:44-51 (1988), and U.S. Pat. Nos. 5,092,885, 5,112,946, 5,192,744, 5,202,352, and 6,573,256. In addition, there are a wide variety of compounds that can be used to inhibit angiogenesis, for example, peptides or agents that block the VEGF-mediated angiogenesis pathway, endostatin protein or derivatives, lysine binding fragments of angiostatin, melanin or melanin-promoting compounds, plasminogen fragments (e.g., Kringles 1-3 of plasminogen), tropoin subunits, antagonists of vitronectin $\alpha_v\beta_3$, peptides derived from Saposin B, antibiotics or analogs (e.g., tetracycline, or neomycin), dienogest-containing compositions, compounds comprising a MetAP-2 inhibitory core coupled to a peptide, the compound EM-138, chalcone and its analogs, and naaladase inhibitors. See, for example, U.S. Pat. Nos. 6,395,718, 6,462,075, 6,465,431, 6,475,784, 6,482,802, 6,482,810, 6,500,431, 6,500,924, 6,518,298, 6,521,439, 6,525,019, 6,538,103, 6,544,758, 6,544,947, 6,548,477, 6,559,126, and 6,569,845.

Depending on the nature of the combinatory therapy, administration of the antibodies of the invention may be continued while the other therapy is being administered and/or thereafter. Administration of the antibodies may be made in a single dose, or in multiple doses. In some instances, administration of the antibodies is commenced at least several days prior to the conventional therapy, while in other instances, administration is begun either immediately before or at the time of the administration of the conventional therapy.

V. Pharmaceutical Compositions and Modes of Administration

In certain embodiments, the subject antibodies of the present invention are formulated with a pharmaceutically acceptable carrier. Such antibodies can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the subject antibodies include those suitable for oral, dietary, topical, parenteral (e.g., intravenous, intraarterial, intramuscular, subcutaneous injection), inhalation (e.g., intrabronchial, intranasal or oral inhalation, intranasal drops), rectal, and/or intravaginal administration. Other suitable methods of administration can also include rechargeable or biodegradable devices and slow release polymeric devices. The pharmaceutical compositions of this invention can also be administered as part of a combinatorial therapy with other agents (either in the same formulation or in a separate formulation).

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of anti-tumor or anti-angiogenesis agent and a carrier and, optionally, one or more accessory ingredients. In general, the formulations can be prepared with a liquid carrier, or a finely divided solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of one or more subject antibodies as an active ingredient.

In solid dosage forms for oral administration (capsules, tablets, pills, dragees, powders, granules, and the like), one or more antibodies of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Methods of the invention can be administered topically, either to skin or to mucosal membranes such as those on the cervix and vagina. This offers the greatest opportunity for direct delivery to tumor with the lowest chance of inducing side effects. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The subject antibodies may be mixed under sterile conditions with a pharmaceutically acceptable carrier, and with any preservatives, buffers, or propellants which may be required. The ointments, pastes, creams and gels may contain, in addition to an antibody, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an antibody, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more antibodies in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more antibodies in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Formulations for intravaginal or rectally administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Exemplification

The invention now being generally described, it will be more readily understood by reference to the following examples, which are included merely for purposes of illustration of certain aspects and embodiments of the present invention, and are not intended to limit the invention.

EXAMPLE 1

Effect of Ephrin B2 and EphB4 Polyclonal Antibodies on Tumor Cell Growth

Two EphB4 polyclonal antibodies (H-200 and N-19) were purchased from Santa Cruz Biotech (Santa Cruz, Calif.). The H-200 antibody (also called sc-5536) has an epitope region corresponding to amino acids 201-400 within an extracellular domain of human EphB4, while the N-19 antibody (also called sc-7285) has an epitope region within an N-terminal extracellular domain of human EphB4. In addition, an Ephrin B2 polyclonal was purchased from R&D Systems (Minneapolis, Minn.).

Figure 6B:
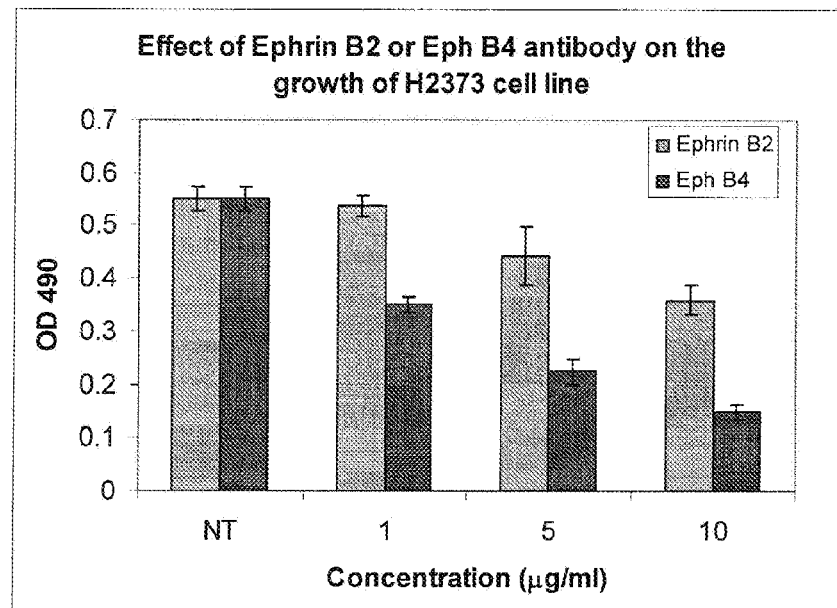
Figure 6C:
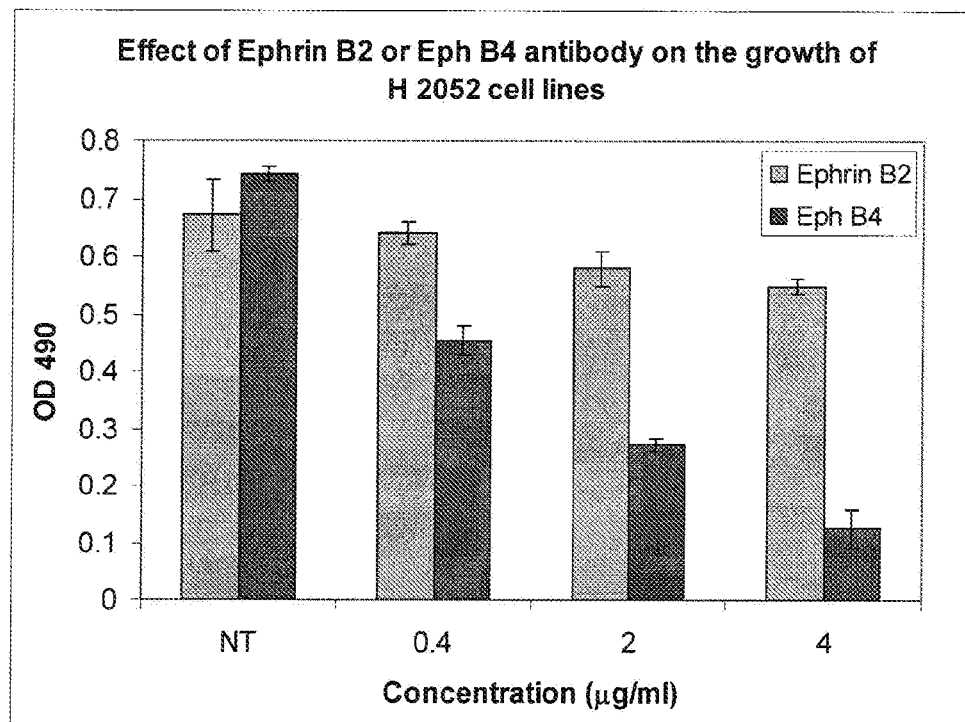

Three mesothelioma cell lines (H28, H2052, and H2373) were obtained from the ATCC (Manassas, Va.) and used to test the anti-tumor activities of these EphB4 and Ephrin B2 polyclonal antibodies. These cells (about 5,000 cells/well) were plated in 48 well plates, and were treated the following day with different concentrations of each antibody. The cell viability assay (MTT) was done on day 4. The effects of the Ephrin B2 and EphB4 polyclonal antibodies on tumor cell growth were shown in FIG. 6.

EXAMPLE 2

Effect of EphB4 Monoclonal Antibodies on Angiogenesis and Tumor Growth

A. Generation and Functional Analysis of EphB4 Antibodies

Anti-EphB4 monoclonal antibodies were raised in mice against the extracellular domain (ECD) of EphB4. An EphB4ECD (see, e.g., FIG. 5) was cloned into expression vectors (e.g., pGEX) to generate EphB4ECD fusion proteins (e.g., GST-ECD). EphB4ECD fusion protein expressed in BL21 *E. coli* was purified by affinity chromatography in the case of GST fusion proteins, the GST domain was cleaved by thrombin. Monoclonal antibody was purified from hybridoma supernatants by Protein A chromatography.

Figure 7:
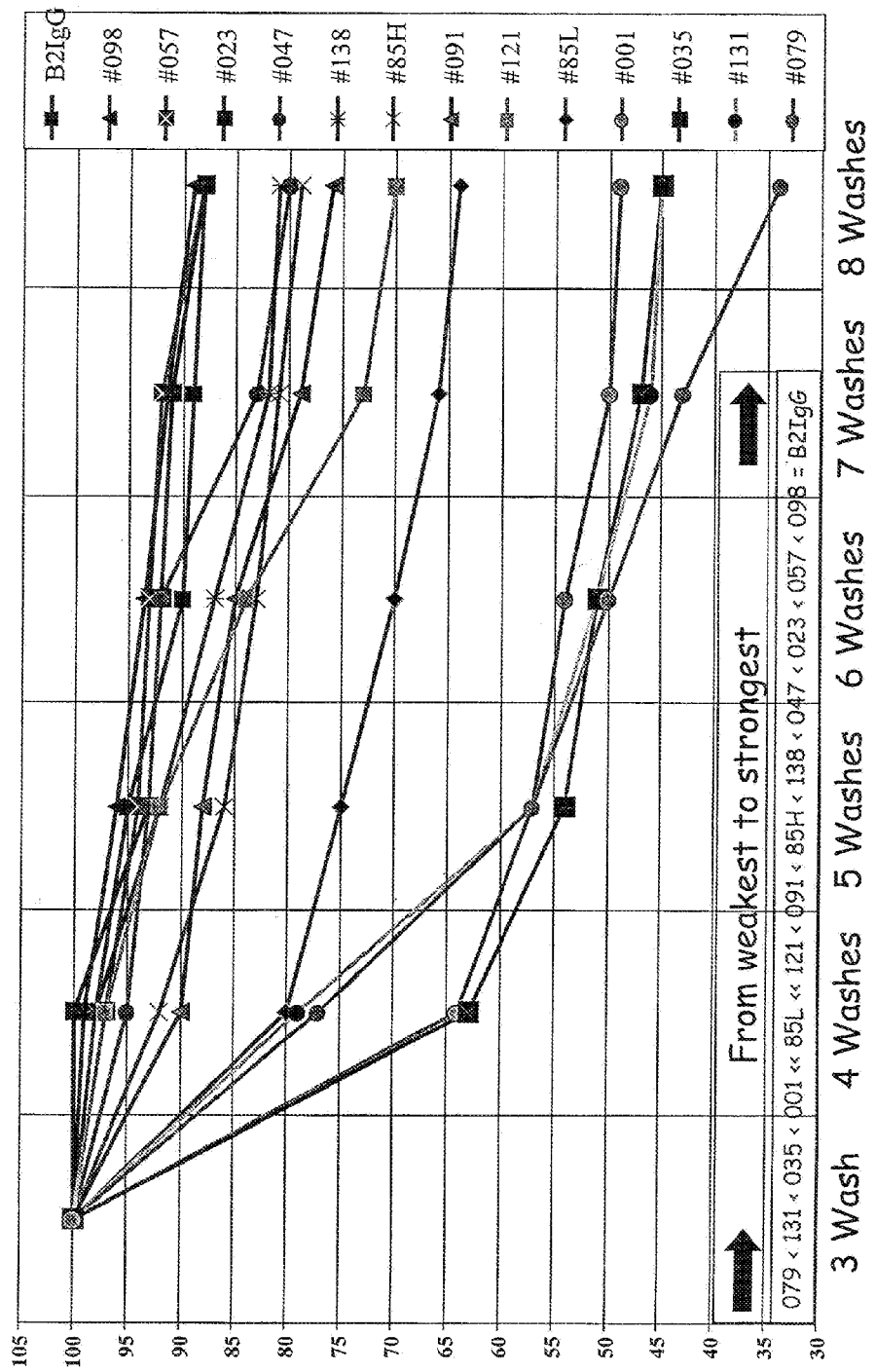
FIG. 7 shows results from affinity tests of EphB4 monoclonal antibodies. The order of the affinity (from weakest to strongest) is shown.

These monoclonal antibodies include EphB4 antibody Nos. 1, 23, 35, 47, 57, 79, 85L, 85H, 91, 98, 121, 131, and 138 (FIG. 5). Antibody mapping studies showed that the epitope domain for each of these antibodies (FIG. 5). Binding affinity of each EphB4 antibody was analyzed and shown in FIG. 7.

Further experiments were carried out to analyze the functional activities of these antibodies, including their abilities to compete with their binding partner such as Ephrin B2, to activate EphB4 tyrosine phosphorylation, to inhibit in vitro tube formation in HUAEC, to inhibit in vivo angiogenesis by matrigel plug assay, to stimulate apoptosis or necrosis in SCC15 tumor cell, and to inhibit SCC15 xenotransplant growth. The results are summarized in Table 1 below.

Apoptosis was assessed by immunohistochemical TUNNEL, and proliferation by BrdU assay. Following surgical removal, tumors were immediately sliced into 2 mm serial sections and embedded in paraffin using standard procedures. Paraffin embedded tissue were sectioned at 5 µl, the wax removed and the tissue rehydrated. The rehydrated tissues were microwave irradiated in antigen retreival solution. Slides were rinsed in PBS, and TUNNEL reaction mixture (Terminal deoxynucleotidyl transferase and flourescein labeled nucleotide solution), and BrdU were added in a humidity chamber completely shielded from light. The TUNNEL and BrdU reaction mixture were then removed, slides were rinsed and anti-flourescein antibody conjugated with horseradish peroxidase

TABLE 1

A summary of activities of EphB4 antibodies.

| Ab. No. | Activation of EphB4 tyrosine phosphorylation | Inhibition of EphB4/Ephrin B2 interaction | Inhibition of HUAEC in vitro tube formation | Inhibition of in vivo angiogenesis (matrigel plug assay) | Stimulation of SCC15 tumor cell apoptosis or necrosis | Inhibition of SCC15 xenotransplant growth | Ab. Subclass |
|---|---|---|---|---|---|---|---|
| 1 | -- | + | + | Nd | N | Nd | IgG2b |
| 23 | -- | + | + | + | A, N | -- | IgG2b |
| 35 | -- | + | + | Nd | A, N | -- | IgG2b |
| 47 | -- | -- | + | -- | Nd | + | IgG3 |
| 57 | -- | -- | -- | -- | Nd | + | IgG3 |
| 79 | -- | + | -- | Nd | A, N | -- | IgG1 |
| 85L | + | -- | -- | -- | Nd | -- | IgG2b |
| 85H | -- | -- | -- | Nd | Nd | Nd | IgG2b |
| 91 | + | -- | -- | Nd | -- | Nd | IgG2a |
| 98 | -- | -- | + | + | Nd | Nd | IgG2a |
| 121 | + | -- | -- | Nd | Nd | -- | IgG1 |
| 131 | + | -- | + | Nd | Nd | + | IgG1 |
| 138 | -- | -- | + | + | A, N | + | IgG2b |

Figure 8:
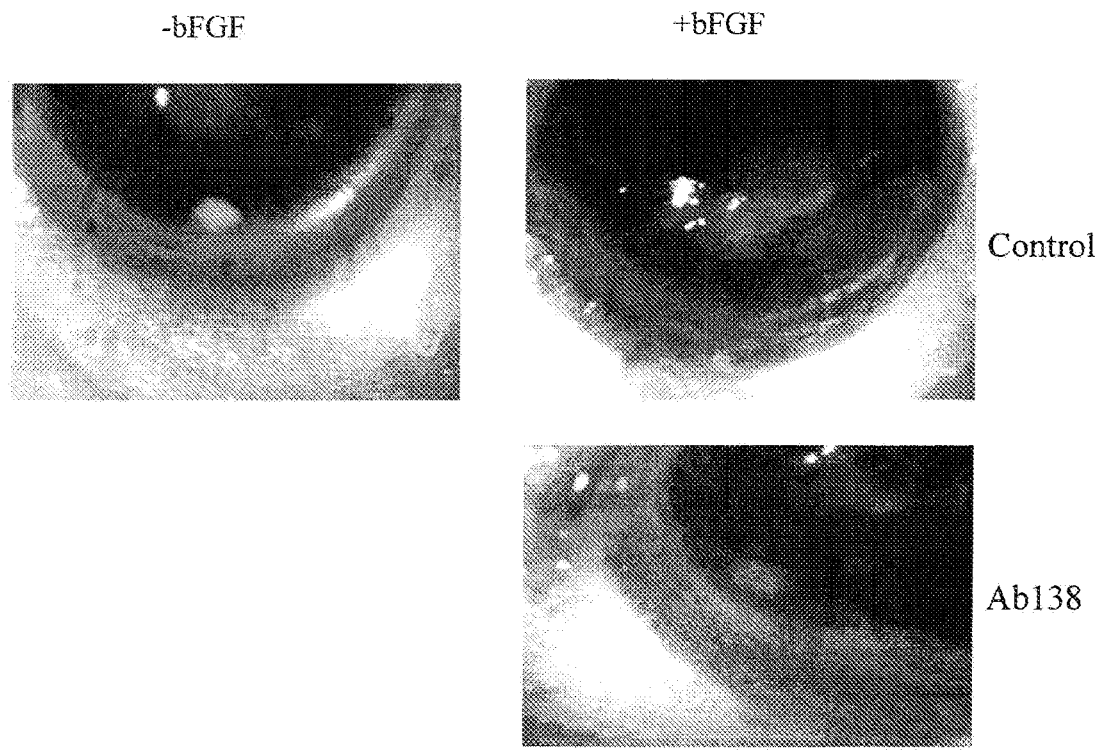
FIG. 8 shows mouse corneal micropocket assay with an exemplary EphB4 antibody (No. 138) in the presence or absence of bFGF.

Nd = not determined (no data provided)
-- = no clear effect
+ = clear effect
A = apoptosis
N = necrosis
A, N = both apoptosis and necrosis The effect of these antibodies on angiogenesis was further analyzed in mouse corneal micropocket assay. For example, EphB4 antibody No. 138 significantly inhibited angiogenesis as shown in FIG. 8.

A representative experiment is shown in FIG. 9 to illustrate the anti-tumor activities of EphB4 antibodies summarized in Table 1. BalbC nude mice were injected subcutaneously with $2.5 \times 10^6$ viable tumor cells (SCC15, a head and neck squamous cell carcinoma line). Tumors were initiated in nu/nu mice by injecting $2.5-5 \times 10^6$ cells premixed with matrigel and Growth factors, and Ab's subcutaneously to initiate tumor xenografts. Mice were opened 14 days after injections. SCC15 is a head and neck squamous cell carcinoma line, B16 is a melanoma cell line, and MCF-7 is a breast carcinoma line. The responses of tumors to these treatments were compared to control treated mice, which receive PBS injections. Animals were observed daily for tumor growth and subcutaneous tumors were measured using a caliper every 2 days. Antibodies #1 and #23 showed significant regression of SCC15 tumor size compared to control, especially with no additional growth factor added, indicating that EphB4 antibodies inhibited the in vivo tumor growth of SCC15 cells.

Another representative experiment is shown in FIG. 10 to illustrate the anti-tumor and anti-angiogenesis activities of EphB4 antibodies summarized in Table 1. Angiogenesis was assessed by CD-31 immunohistochemistry. Tumor tissue sections from treated and untreated mice were stained for CD31. was added. After incubation and rinsing, 3,3' diaminobenzidine was added. Masson's Trichrome and Hematoxylin and Eosin were also used to stain the slides to visualize morphology. Masson's Trichrome allows to visualize necrosis and fibrosis. The tumor gets blood support from tumor/skin, muscle boundary. As tumor grows, inner regions get depleted of nutrients. This leads to necrosis (cell death), preferably at the tumor center. After cells die, (tumor) tissue gets replaced with fibroblastic tissue. Slides were visualized under 20-fold magnification with digital images acquired. A different morphology was obtained on SCC tumors with each antibody administered. Ab #1 showed an increase in necrosis and fibrosis but not apoptosis. Ab #23 showed an increase in apoptosis, necrosis and fibrosis and a decrease in vessel infiltration. Ab #35 showed an increase in necrosis and fibrosis, and a small increase in apoptosis and a decrease in vessel infiltration. Ab #79 showed a large increase in apoptosis, and necrossis and fibrosis. Ab #91 showed no change in apoptosis but an increase in proliferation. And Ab #138 showed an increase in apoptosis, necrosis, fibrosis and a decrease in proliferation and vessel infiltration. Tumors treated with control PBS displayed abundant tumor density and a robust angiogenic response. Tumors treated with EphB4 antibodies displayed a decrease in tumor cell density and a marked inhibition of tumor angiogenesis in regions with viable tumor cells, as well as tumor necrosis and apoptosis. These results show that EphB4 antibodies caused apoptosis, necrosis and decreased angiogenesis in SCC15, head and neck carcinoma tumor type.

A further representative experiment is shown in FIG. 11 to illustrate the anti-tumor activities of EphB4 antibodies summarized in Table 1. Alternate day treatment with EphB4 monoclonal antibody or an equal volume of PBS as control were initiated on day 4, after the tumors have established, and continued for 14 days. Systemic administration was administered either IP or SC with no significant difference. All the experiments were carried out in a double-blind manner to eliminate investigator bias. Mice were sacrificed at the conclusion of the two week treatment period. Tumors were harvested immediately postmortem and fixed and processed for immunohistochemistry. EphB4 antibodies 40 mg per kg body weight were administered. Treatment with EphB4 antibody significantly inhibited human SCC tumor growth compared with control-treated mice ($p<0.05$). Treatment with EphB4 antibody significantly inhibited tumor weight compared with control-treated mice ($p<0.05$). These results show that systemic administration of antibodies on xenografts led to tumor regression in SCC15 tumor xenografts.

EXAMPLE 3

Materials and Methods

1) Immunohistochemistry

Formalin-fixed tissue sections were deparaffinized and incubated with 10% goat serum at −70° C. for 10 minutes and incubated with the EphB4 monoclonal antibody 4° C. overnight. Isotype-specific rabbit IgG was used as control. The immunoreactivity for these receptors was revealed using an avidin-biotin kit from Vector Laboratories. Peroxidase activity was revealed by the diaminobenzidine (Sigma) cytochemical reaction. The slides were then counterstained with 0.12% methylene blue or H&E. For frozen sections, OCT-embedded tissues were sectioned at 5 μm and fixed in phosphate-buffered 4% paraformaldehyde. Sections were washed for 3×5 min in PBS and endogenous peroxidase was blocked by incubation in 0.3% $H_2O_2$ in PBS for 10 min at room temperature. Sections were incubated with Eph4 (C-16) antibody (1:50) for 1 h at room temperature followed by three washes in PBS and incubation with donkey anti-goat secondary antibody (Santa Cruz Biotech.) for 1 h at room temperature. After three washes in PBS, peroxidase activity was localized by incubation in DAB substrate solution (Vector Laboratories, Inc. Burlingame Calif.) for 10 min at room temperature. Sections were counterstained with Hematoxylin for 20 s, dehydrated and mounted. Negative control for staining was substitution of normal goat serum for primary antibody.

2) Western Blot

Whole cell lysates were prepared using Cell Lysis Buffer (GeneHunter, Basgvukke Tenn.) supplemented with protease inhibitor cocktail (Pierce, Rockford Ill.), unless otherwise noted. Total protein was determined using the DC reagent system (Bio-Rad, Hercules Calif.). Typically, 20 μg whole cell lysate was run on 4-20% Tris-Glycine gradient gel. The samples were electro-transferred to PVDF membrane and the non-specific binding was blocked in TBST buffer (0.5 mM Tris-HCl, 45 mM NaCl, 0.05% Tween-20, pH 7.4) containing 5% non-fat milk. Membranes were first probed with primary antibody overnight, stripped with Restore™ Western Blot stripping buffer (Pierce, Rockford Ill.) and reprobed with β-actin to confirm equivalent loading and transfer of protein. Signal was detected using SuperSignal West Femto Maximum Sensitivity Substrate (Pierce).

3) Tyrosine Kinase Phosphorylation Analysis

Cells growing in 60 mm dishes were either serum starved (1% FBS supplemented RPMI 1640, 24 hours) or cultured in normal conditions (10% FBS) and then treated with or without 1 μg/ml mouse ephrin B2/$F_c$ for 10 min to activate EphB4 receptor. Cleared cell lysates were incubated with EphB4 monoclonal antibody overnight at 4° C. Antigen-antibody complex was immunoprecipitated by the addition of 100 μl of Protein G-Sepharose in 20 mM sodium phosphate, pH 7.0 with incubation overnight at 4° C. Immunoprecipitates were analyzed by Western blot with phosphotyrosine (pTyr) specific antibody (Upstate, clone 4G10) at 1:1000 dilution followed by incubation with protein G-HRP (Bio-Rad) at 1:5000 dilution. To monitor immunoprecipitation efficiency, a duplicate membrane was probed with EphB4 specific monoclonal antibody.

4) Cell Culture

Normal HUVECs were obtained from Cambrex (BioWhittaker) and maintained in EBM2 medium supplemented with 0.1 mg/ml endothelial growth supplement (crude extract from bovine brain), penicillin (50 U/ml), streptomycin (50 U/ml), 2 mmol/l glutamine and 0.1 mg/ml sodium heparin. Aliquots of cells were preserved frozen between passages 1 and 3. For all experiments, HUVECs were used at passages 4 or below and collected from a confluent dish.

NCI H28 and NCI H2373 mesothelioma cell lines were obtained from the ATCC (Manassas, Va.). Cells were maintained in RPMI 1640 media supplemented with 10% heat-inactivated fetal bovine serum (FBS; Life Technologies, Gaithersburg, Md.) and antibiotics. Primary cells were obtained from pleural effusion of patients with mesothelioma.

5) Endothelial Cell Tube Formation Assay

Matrigel (60 μl of 10 mg/ml; Collaborative Lab, Cat. No. 35423) was placed in each well of an ice-cold 96-well plate. The plate was allowed to sit at room temperature for 15 minutes then incubated at 37° C. for 30 minutes to permit Matrigel to polymerize. In the mean time, human umbilical vein endothelial cells were prepared in EGM-2 (Clonetic, Cat. No. CC3162) at a concentration of $2 \times 10^5$ cells/ml. Cells (500 μl) and the test EphB4 antibody were mixed and 200 μl of this suspension were placed in duplicate on the polymerized Matrigel. After 24 h incubation, triplicate pictures were taken for each concentration using a Bioquant Image Analysis system. Protein addition effect ($IC_{50}$) was assessed compared to untreated controls by measuring the length of cords formed and number of junctions.

6) Cell Migration Assay

Chemotaxis of HUVECs to VEGF was assessed using a modified Boyden chamber, transwell membrane filter inserts in 24 well plates, 6.5 mm diam, 8 μm pore size, 10 μm thick matrigel coated, polycarbonate membranes (BD Biosciences). The cell suspensions of HUVECs ($2 \times 10^5$ cells/ml) in 200 μl of EBM were seeded in the upper chamber and the test EphB4 antibodies were added simultaneously with stimulant (VEGF or bFGF) to the lower compartment of the chamber and their migration across a polycarbonate filter in response to 10-20 ng/ml of VEGF with or without 100 nM-1 μM test compound was investigated. After incubation for 4-24 h at 37° C., the upper surface of the filter was scraped with swab and filters were fixed and stained with Diff Quick. Ten random fields at 200× mag were counted and the results expressed as mean # per field. Negative unstimulated control values were subtracted from stimulated control and protein treated sample values and the data was plotted as mean migrated cell±S.D. $IC_{50}$ was calculated from the plotted data.

7) Growth Inhibition Assay

HUVEC ($1.5 \times 10^3$ cells) were plated in a 96-well plate in 100 µl of EBM-2 (Clonetic, Cat. No. CC3162). After 24 hours (day 0), the test EphB4 antibody is added to each well at the desired concentration in EBM-2 medium. On day 0, one plate was stained with 0.5% crystal violet in 20% methanol for 10 minutes, rinsed with water, and air-dried. The remaining plates were incubated for 72 h at 37° C. After 72 h, plates were stained with 0.5% crystal violet in 20% methanol, rinsed with water and air-dried. The stain was eluted with 1:1 solution of ethanol: 0.1 M sodium citrate (including day 0 plate), and absorbance measured at 540 nm with an ELISA reader (Dynatech Laboratories). Day 0 absorbance was subtracted from the 72 h plates and data is plotted as percentage of control proliferation (vehicle treated cells). $IC_{50}$ value was calculated from the plotted data.

8) Murine Matrigel Plug Angiogenesis Assay

In vivo angiogenesis was assayed in mice as growth of blood vessels from subcutaneous tissue into a Matrigel plug containing the test sample. Matrigel rapidly forms a solid gel at body temperature, trapping the factors to allow slow release and prolonged exposure to surrounding tissues. Matrigel (8.13 mg/ml, 0.5 ml) in liquid form at 4° C. was mixed with Endothelial Cell Growth Supplement (ECGS), test EphB4 antibodies plus ECGS or Matrigel plus vehicle alone (PBS containing 0.25% BSA). Matrigel (0.5 ml) was injected into the abdominal subcutaneous tissue of female nu/nu mice (6 wks old) along the peritoneal mid line. There were 3 mice in each group. The animals were cared for in accordance with institutional and NIH guidelines. At day 6, mice were sacrificed and plugs were recovered and processed for histology. Typically, the overlying skin was removed, and gels were cut out by retaining the peritoneal lining for support, fixed in 10% buffered formalin in PBS and embedded in paraffin. Sections of 3 µm were cut and stained with H&E or Masson's trichrome stain and examined under light microscope.

9) Mouse Corneal Micropocket Assay

Mouse corneal micropocket assay was performed according to that detailed by Kenyon et al., 1996. Briefly, hydron pellets (polyhydroxyethylmethacrylate [polyHEMA], Interferon Sciences, New Brunswick, N.J., U.S.A.) containing either 90 ng of bFGF (R&D) or 180 ng of VEGF (R&D Systems, Minneapolis, Minn., U.S.A.) and 40 µg of sucrose aluminium sulfate (Sigma) were prepared. Using an operating microscope, a stromal linear keratotomy was made with a surgical blade (Bard-Parker no. 15) parallel to the insertion of the lateral rectus muscle in an anesthetized animal. An intrastromal micropocket was dissected using a modified von Graefe knife (2"30 mm). A single pellet was implanted and advanced toward the temporal corneal limbus (within 0±7±1±0 mm for bFGF pellets and 0±5 mm for VEGF pellets). The difference in pellet location for each growth factor was determined to be necessary given the relatively weaker angiogenic stimulation of VEGF in this model. Antibiotic ointment (erythromycin.) was then applied to the operated eye to prevent infection and to decrease surface irregularities. The subsequent vascular response was measured extending from the limbal vasculature toward the pellet and the contiguous circumferential zone of neovascularization. Data and clinical photos presented here were obtained on day 6 after pellet implantation, which was found to be the day of maximal angiogenic response.

10) In Vitro Invasion Assay

"Matrigel" matrix-coated 9-mm cell culture inserts (pore size, 8 µm; Becton Dickinson, Franklin Lakes, N.J.) were set in a 24-well plate. The HUVEC cells were seeded at a density of $5 \times 10^3$ cells per well into the upper layer of the culture insert and cultured with serum-free EBM in the presence of the test EphB4 antibodies for 24 h. The control group was cultured in the same media without EphB4 antibodies. Then 0.5 ml of the human SCC15 cell line, conditioned medium was filled into the lower layer of the culture insert as a chemo-attractant. The cells were incubated for 24 h, then the remaining cells in the upper layer were swabbed with cotton and penetrating cells in the lower layer were fixed with 5% glutaraldehyde and stained with Diff Quick. The total number of cells passing through the Matrigel matrix and each 8 µm pore of the culture insert was counted using optical microscopy and designated as an invasion index (cell number/area).

11) SCC15 Tumor Growth in Mice

Subcutaneously inject logarithmically growing SCC15, head and neck squamous cell carcinoma cell line, at $5 \times 10^6$ cell density; with or without the test EphB4 antibody in the presence or absence of human bFGF, into athymic Balb/c nude mice, along with Matrigel (BD Bioscience) synthetic basement membrane (1:1 v/v), and examine tumors within 2 weeks. Tumor volumes in the test EphB4 antibody group, in the presence and absence of growth factor after implantation were three-fold smaller than those in the vehicle groups. There was no difference in body weight between the groups. Immunohistochemical examination of cross-sections of resected tumors and TUNEL-positive apoptosis or necrosis, CD34 immunostaining, and BrdU proliferation rate will be performed, after deparaffinized, rehydrated, and quenched for endogenous peroxidase activity, and after 10 min permeabilization with proteinase K. Quantitative assessment of vascular densities will also be performed. Local intratumoral delivery or IV delivery of the test EphB4 antibody will also be performed twice a week.

30 athymic nude mice, BALB/c (nu/nu), were each injected with $1 \times 10^6$ B16 melanoma cells with 0.1 ml PBS mixed with 0.1 ml matrigel or $1.5 \times 10^6$ SCC15 cells resuspended in 200 µl of DMEM serum-free medium and injected subcutaneously on day 0 on the right shoulder region of mice. Test EphB4 antibodies were injected intravenously or subcutaneously, around the tumor beginning on day 1 at a loading dose of 4 µg/mg, with weekly injections of 2 µg/mg (10 µg/g, 50 µg/kg/day), and at 2 weeks post-inoculation. Mice are sacrificed on Day 14. Control mice received PBS 50 µl each day.

12) Tumor Formation in Nude Mice

All animals were treated under protocols approved by the institutional animal care committees. Cancer cells ($5 \times 10^6$) were subcutaneously inoculated into the dorsal skin of nude mice. When the tumor had grown to a size of about 100 mm³ (usually it took 12 days), the test EphB4 antibody was either intraperitoneally or subcutaneously injected once/day, and tumorigenesis was monitored for 2 weeks. Tumor volume was calculated according to the formula $a^2 \times b$, where a and b are the smallest and largest diameters, respectively. A Student's t test was used to compare tumor volumes, with $P<0.05$ being considered significant.

13) Quantification of Microvessel Density

Tumors were fixed in 4% formaldehyde, embedded in paraffin, sectioned by 5 µm, and stained with hematoxylineosin. Vessel density was semi-quantitated using a computer-based image analyzer (five fields per section from three mice in each group).

Incorporation by Reference

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. An isolated monoclonal antibody or antigen binding portion thereof that binds to an epitope situated within amino acids 430-537 of SEQ ID NO: 1 and promotes apoptosis in a tumor cell.

2. The isolated antibody or antigen binding portion thereof of claim 1, which binds to the second fibronectin-like domain (FND2) of EphB4.

3. The isolated antibody or antigen binding portion thereof of claim 1, wherein the antibody or antigen binding portion thereof comprises at least one CDR portion derived from antibody 47.

4. The isolated antibody or antigen binding portion thereof of claim 1, which is a humanized antibody.

5. The isolated antibody or antigen-binding portion thereof of claim 1, wherein the antibody or antigen-binding portion thereof inhibits the formation of tubes by cultured endothelial cells.

6. The isolated antibody or antigen-binding portion thereof of claim 1, wherein the antibody or antigen-binding portion thereof inhibits the vascularization of a tissue in vivo.

7. The isolated antibody or antigen-binding portion thereof of claim 6, wherein the antibody or antigen-binding portion thereof inhibits the vascularization of tissue implanted in the cornea of an animal.

8. The isolated antibody or antigen-binding portion thereof of claim 6, wherein the antibody or antigen-binding portion thereof inhibits the vascularization of a Matrigel tissue plug implanted in an animal.

9. The isolated antibody or antigen-binding portion thereof of claim 1, wherein the antibody or antigen-binding portion thereof decreases the growth of a human tumor xenograft in a mouse.

10. The antibody of claim 1, wherein the monoclonal antibody is clinically acceptable for administration to a human.

11. An isolated antibody or antigen-binding portion thereof of claim 1, wherein the isolated antibody or antigen-binding portion thereof is covalently linked to an additional functional moiety.

12. The isolated antibody or antigen-binding portion thereof of claim 11, wherein the additional functional moiety is a label.

13. The isolated antibody or antigen-binding portion thereof of claim 12, wherein the label is suitable for detection by a method selected from: fluorescence detection methods, positron emission tomography detection methods and nuclear magnetic resonance detection methods.

14. The isolated antibody or antigen-binding portion thereof of claim 13, wherein the label is selected from: a fluorescent label, a radioactive label, and a label having a distinctive nuclear magnetic resonance signature.

15. The isolated antibody or antigen-binding portion thereof of claim 11, wherein the additional functional moiety confers increased serum half-life on the antibody or antigen binding portion thereof.

16. The isolated antibody or antigen-binding portion thereof of claim 15, wherein the additional functional moiety comprises a polyethylene glycol (PEG) moiety.

17. A pharmaceutical preparation comprising the isolated antibody or antigen binding portion thereof of claim 1.

18. A method for treating cancer in a patient, comprising administering the isolated antibody or antigen binding portion thereof of claim 1 to a patient in need thereof.

19. The method of claim 18, wherein the cancer is selected from colon carcinoma, breast tumor, mesothelioma, prostate tumor, squamous cell carcinoma, Kaposi's sarcoma, and leukemia.

20. A method for inhibiting angiogenesis in a patient, comprising administering the isolated antibody or antigen binding portion thereof of claim 1 to a patient in need thereof.

21. A method for inhibiting macular degeneration in a patient, comprising administering the isolated antibody or antigen binding portion thereof of claim 1 to a patient in need thereof.

22. A hybridoma that produces an antibody of claim 1.

23. The hybridoma of claim 22, wherein the hybridoma produces antibody 47.

* * * * *